US012740999B2

United States Patent
(12) United States Patent
Toscano et al.

(10) Patent No.: US 12,740,999 B2
(45) Date of Patent: Sep. 22, 2026

(54) SOLID-GAS REACTION TO GENERATE NITROXYL (HNO) IN THE GAS PHASE

(71) Applicants: The Johns Hopkins University, Baltimore, MD (US); Universidad de Buenos Aires, Buenos Aires (AR); CONSEJO NACIONAL DE INVESTGACIONES CIENTFICAS Y TECNICAS CONICET, Buenos Aires (AR)

(72) Inventors: John Pasquale Toscano, Baltimore, MD (US); Jessica Zarenkiewicz, Baltimore, MD (US); Guillermo Alejandro Carrone, Buenos Aires (AR); Agostina Maria Mazzeo, Buenos Aires (AR); Ernesto Jose Marceca, Buenos Aires (AR); Juan Pellegrino, Buenos Aires (AR); Fabio Ariel Doctorovich, Buenos Aires (AR); Sebastian Suarez, Buenos Aires (AR); Paola E. Vargas, Buenos Aires (AR)

(73) Assignees: THE JOHNS HOPKINS UNIVERSITY, Baltimore, MD (US); Universidad de Buenos Aires, Buenos Aires (AR); CONSEJO NACIONAL DE INVESTGACIONES CIENTFICAS Y TECNICAS CONICET, Buenos Aires (AR)

( * ) Notice: Subject to any disclaimer, the term of this patent is extended or adjusted under 35 U.S.C. 154(b) by 274 days.

(21) Appl. No.: 18/560,588

(22) PCT Filed: May 17, 2022

(86) PCT No.: PCT/US2022/029572
§ 371 (c)(1),
(2) Date: Nov. 13, 2023

(87) PCT Pub. No.: WO2022/245781
PCT Pub. Date: Nov. 24, 2022

(65) Prior Publication Data

US 2024/0269164 A1 Aug. 15, 2024

Related U.S. Application Data

(60) Provisional application No. 63/189,534, filed on May 17, 2021.

(51) Int. Cl.
*A61K 33/00* (2006.01)
*C01B 21/20* (2006.01)
*C01C 1/02* (2006.01)

(52) U.S. Cl.
CPC .............. *A61K 33/00* (2013.01); *C01B 21/20* (2013.01); *C01C 1/026* (2013.01)

(58) Field of Classification Search
CPC ...... A61K 33/00; C01B 21/20; C01B 21/082; C01C 1/026; A61P 9/12
See application file for complete search history.

(56) References Cited

U.S. PATENT DOCUMENTS 6,936,639 B2 8/2005 Wink et al.
10,487,049 B2 11/2019 Toscano et al.
(Continued)

FOREIGN PATENT DOCUMENTS

WO WO-2020136414 A1 7/2020

OTHER PUBLICATIONS

Ellis et al. (British Journal of Pharmacology (2000) 129, 315-322) (Year: 2000).*
(Continued)

*Primary Examiner* — Ernst V Arnold
(74) *Attorney, Agent, or Firm* — Casimir Jones, SC; Jeffrey W. Childers

(57) ABSTRACT

Disclosed is a method for generating nitroxyl (HNO) in the gas phase, the method comprising contacting a solid base-catalyzed HNO donor with a gaseous base; or a solid acid-catalyzed HNO donor with a gaseous acid; to form
(Continued)

HNO in the gas phase and methods of treating a disease or condition responsive to HNO therapy with the HNO formed in the gas phase.

7 Claims, 20 Drawing Sheets

(56) References Cited

U.S. PATENT DOCUMENTS

2012/0285449 A1* 11/2012 Fine .................... A61M 16/122 128/203.12
2020/0230330 A1 7/2020 Jensen et al.

OTHER PUBLICATIONS

Kumar et al. (Nitric Oxide 77 (2018) 96-105) (Year: 2018).*
Saurez et al. (J. Am. Chem. Soc. 2015, 137, 4720-4727). (Year: 2015).*
Heinecke et al. (J. Am. Chem. Soc. 2013, 135, 4007-4017) (Year: 2013).*
Paolocci et al. (Pharmacol Ther. Feb. 2007 ; 113(2): 442-458) (Year: 2007).*
Moller et al. ( J. Biol. Chem. (2019) 294(40) 14776-14802) (Year: 2019).*
Adak S., et al., "Arginine Conversion to Nitroxide by Tetrahydrobiopterin-free Neuronal Nitric-oxide Synthase", Implications for Mechanism, The Journal of Biological Chemistry, Oct. 27, 2000, vol. 275, No. 43, pp. 33554-33561.
Adas S.K., et al., "Synthesis and HNO Donating Properties of the Piloty's Acid Analogue Trifluoromethanesulphonylhydroxamic Acid: Evidence for Quantitative Release of HNO at Neutral pH Conditions", Chemistry—A European Journal, May 23, 2018, vol. 24, No. 29, pp. 7330-7334, 6 Pages.
Aizawa K., et al., "Piloty's Acid Derivative with Improved Nitroxyl-releasing Characteristics", Bioorgaic & Medicinal Chemistry Letters, Apr. 15, 2013, vol. 23, No. 8, pp. 2340-2343.
Arnold W.P., et al., "Nitric Oxide Activates Guanylate Cyclase and Increases Guanosine 3':5'-Cyclic Monophosphate Levels in Various Tissue Preparations", Proceedings of the National Academy of Sciences of the United States of America, Aug. 1977, vol. 74, No. 8, pp. 3203-3207.
Badesch D.B., et al., "Diagnosis and Assessment of Pulmonary Arterial Hypertension", Journal of the American College of Cardiology, Jun. 30, 2009, vol. 54, No. 1, pp. S55-S66.
Basudhar D., et al., "Advances in Breast Cancer Therapy Using Nitric Oxide and Nitroxyl Donor Agents", Redox-Active Therapeutics, 2016, pp. 377-403.
Basudhar D., et al., "HNO Donors: Angeli's Salt and Related Diazeniumdiolates", The Chemistry and Biology of Nitroxyl (HNO), Elsevier, 2017, pp. 11-36.
Bonner F.T., et al., "Kinetic, Isotopic, and Nitrogen-15 NMR Study of N-Hydroxybenzenesulfonamide Decomposition: An Nitrosyl Hydride (HNO) Source Reaction", Inorganic Chemistry, 1992, vol. 31, No. 12, pp. 2514-2519.
Bouzamondo A., et al., "Beta-Blocker Treatment in Heart Failure", Blackwell Science Fundamental & Clinical Pharmacology, Apr. 2001, vol. 15, No. 2, pp. 95-109.
Bristow M.R., et al., "Inotropes and Beta-Blockers: Is there A Need for New Guidelines?", Journal of Cardiac Failure, Jun. 2001, vol. 7, No. 2, Suppl 1, pp. 8-12.
Carrone G., et al., "Solid-gas Reactions for Nitroxyl (HNO) Generation in the Gas Phase," Journal of Inorganic Biochemistry, Jul. 9, 2021, vol. 223, No. 111535, DOI: https://doi.org/10.1016/j.jinorgbio.2021.111535, XP093011317, pp. 1-5.
Carrone G., et al., "Rapid Generation of HNO Induced by Visible Light", Chemical Communications, May 9, 2017, vol. 53, No. 38, pp. 5314-5317, 5 pages.
Chazotte-Aubert L., et al., "Cytotoxicity and Site-specific DNA Damage Induced by Nitroxyl Anion (NO(−)) in the Presence of Hydrogen Peroxide", Implications for Various Pathophysiological Conditions, The Journal of Biological Chemistry, Jul. 23, 1999, vol. 274, No. 30, pp. 20909-20915.
Chouchani E.T., et al., "Cardioprotection by S-Nitrosation of a Cysteine Switch on Mitochondrial Complex I", Nature Medicine, Jun. 2013, vol. 19, No. 6, pp. 753-759, 10 Pages.
Cline M.R., et al., "Detection of Nitroxyl (HNO) by Membrane Inlet Mass Spectrometry", Free Radical Biology Medicine, May 15, 2011, vol. 50, No. 10, pp. 1274-1279.
Clyne M.A.A., et al., "Mechanism of Chemiluminescent Reactions Involving Nitric Oxide-the H + NO Reaction", Discuss, Faraday Society, 1962, vol. 33, pp. 139-148.
Clyne M.A.A., et al., "Reaction of Nitrogen Dioxide with Active Nitrogen", Transactions of the Faraday Society, 1961, vol. 57, No. 69, 10 pages.
D'Andrea A.D., "Mechanisms of PARP Inhibitor Sensitivity and Resistance", DNA Repair, Nov. 2018, vol. 71, No. 172-176, 5 Pages.
Demaster E.G., et al., "Mechanisms of Inhibition of Aldehyde Dehydrogenase by Nitroxyl, the Active Metabolite of the Alcohol Deterrent Agent Cyanamide", Biochemical Pharmacology, Jun. 15, 1998, vol. 55, No. 12, pp. 2007-2015.
Denis M., "Interferon-Gamma-Treated Murine Macrophages Inhibit Growth of Tubercle Bacilli via the Generation of Reactive Nitrogen Intermediates", Cell Immunol, Jan. 1991, vol. 132, No. 1, pp. 150-157.
Doctorovich F., et al., "Reactions of HNO with Metal Porphyrins: Underscoring the Biological Relevance of HNO", Accounts Of Chemical Research, Oct. 21, 2014, vol. 47, No. 10, pp. 2907-2916.
Doctorovich F., et al., "The Chemistry and Biology of Nitroxyl (HNO)", Elsevier, 2016, vol. 53, TOC only, 9 Pages.
Dutton A.S., et al., "Mechanisms of HNO and NO Production from Angeli's Salt: Density Functional and CBS-QB3 Theory Predictions", Journal of the American Chemical Society, 2004, vol. 126, No. 12, pp. 3795-3800, 10.1021/ja0391614.
El-Bourawi., et al., "Application of Vacuum Membrane Distillation for Ammonia Removal", Journal Of Membrane Science, 2007, vol. 301, No. 1-2, pp. 200-209.
Feigin V.L., et al., "Prevention of Stroke: A Strategic Global Imperative", Nature Review, Neurology, Sep. 2016, vol. 12, No. 9, pp. 501-512, pp. 1-12.
Flores-Santana W., et al., "The Specificity of Nitroxyl Chemistry Is Unique Among Nitrogen Oxides in Biological Systems", Antioxid & Redox Signal, May 1, 2011, vol. 14, No. 9, pp. 1659-1674, 17 Pages.
Fukuto J.M., et al., "A Recent History of Nitroxyl Chemistry, Pharmacology and Therapeutic Potential", British Journal of Pharmacology, Jan. 2019, vol. 176, No. 2, pp. 135-146.
Fukuto J.M., et al., "Conversion of Nitroxyl (HNO) to Nitric Oxide (NO) in Biological Systems: The Role of Physiological Oxidants and Relevance to the Biological Activity of HNO", Biochemical and Biophysical Research Communications, Oct. 29, 1993, vol. 196, No. 2, pp. 707-713.
Fukuto J.M., et al., "HNO Signaling Mechanisms", Antioxidants & Redox Signaling, May 1, 2011, vol. 14, No. 9, pp. 1649-1657, 11 Pages.
Fukuto J.M., et al., "Involvement of Nitroxyl (HNO) in the Cyanamide-induced Vasorelaxation of Rabbit Aorta", Biochemical Pharmacology, Mar. 2, 1994, vol. 47, No. 5, pp. 922-924.
Galizia J., et al., "Evaluation of Nitroxyl Donors' Effect on Mycobacteria", Tuberculosis, Mar. 2018, vol. 109, pp. 35-40.
Galizia J., et al., "Reactive Nitrogen and Oxygen Species: Friend or Foe in the Tuberculosis Fight" Tuberculosis, Dec. 2018, vol. 113, pp. 175-176, 5 Pages.
Gallego C.M., et al., "Azanone (HNO): Generation, Stabilization and Detection," Chemical Science, Jul. 5, 2021, vol. 12, pp. 10410-10425, DOI: https://doi.org/10.1039/D1SC02236A, XP093011320.
Geethakumari P.R., et al., "Higher Rates of Relapse in Maternal Recipients of Haploidentical Hematopoietic Stem Cell Transplantaion from Adult Offspring Donors for AML and Myelodysplastic Syndrome", Bone Marrow Transplantaion, 2017, vol. 52, pp. 1465-1467.

(56) References Cited

OTHER PUBLICATIONS

Geethakumari P.R., et al., "PARP Inhibitors in Prostate Cancer", Current Treatment Options in Oncology, Jun. 2017, vol. 18, No. 37, 16 Pages.
Guo Y., et al., "Advances in Research on Treatment of Heart Failure with Nitrosyl Hydrogen", Heart Failure Reviews, Nov. 2019, vol. 24, No. 6, pp. 941-948, 8 Pages.
Guthrie D.A., et al., "Catch-and-Release" of HNO with Pyrazolones, The Journal Of Organic Chemistry, Feb. 6, 2015, vol. 80, No. 3, pp. 1338-1348.
Hare J.M., et al., "Nitric Oxide Inhibits the Positive Inotropic Response to Beta-adrenergic Stimulation in Humans with Left Ventricular Dysfunction", Circulation, Oct. 15, 1995, vol. 92, No. 8, pp. 2198-2203, pp. 1-13.
Hart C.Y.T., et al., "Differential Effects of Natriuretic Peptides and NO on LV Function in Heart Failure and Normal Dogs", American Journal of Physiology—Heart and Circulatory Physiology, 2001, vol. 281, pp. H146-H154.
Harteck P., "The preparation of HNO and [HNO]n", Reports of the German Chemical Society (A and B Series), Mar. 1, 1933, vol. 66, No. 3, pp. 423-426.
Hartman J.C., et al., "Intravenous Infusion of the Novel HNO Donor BMS-986231 Is Associated With Beneficial Inotropic, Lusitropic, and Vasodilatory Properties in 2 Canine Models of Heart Failure", JACC Basic Translation Science, Nov. 12, 2018, vol. 3, No. 5, pp. 625-638.
Heinecke J.L., et al., "Nitrite Reduction Mediated by Heme Models. Routes to NO and HNO?", Journal Of The American Chemical Society, Mar. 13, 2013, vol. 135, No. 10, pp. 4007-4017.
Hirst D.G., et al., "Nitrosative Stress As a Mediator of Apoptosis: Implications for Cancer Therapy", Current Pharmaceutical Design, Jan. 2010, vol. 16, No. 1, pp. 45-55.
Ingall T.J., et al., "Preventing Ischemic Stroke", Current Approaches to Primary and Secondary Prevention, Postgraduate Medicine, May 15, 2000, vol. 107, No. 6, pp. 34-36, 39-42, 47-50.
International Search Report and Written Opinion for International Application No. PCT/US2022/029572, mailed Sep. 29, 2022, 10 Pages.
Irvine J.C., et al., "Nitroxyl (HNO): the Cinderella of the Nitric Oxide Story," Trends in Pharmacological Sciences, Elsevier, Haywarth, GB, Oct. 1, 2008, vol. 29, No. 12, GB, pp. 601-608, DOI: 10.1016/j.tips.2008.08.005, ISSN: 0165-6147,XP025684683, Dec. 1, 2008.
Jamaati H., et al., "Nitric Oxide in the Pathogenesis and Treatment of Tuberculosis", Frontiers in Microbiology, Oct. 12, 2017, vol. 8, No. 2008, doi:10.3389/fmicb.2017.02008, pp. 1-11.
Kashfi K., "Nitric Oxide in Cancer and Beyond", Biochemical Pharmacology, Jun. 2020, vol. 176, No. 114006, pp. 1-7.
Keceli G., et al., "Nitroxyl (HNO) Targets Phospholamban Cysteines 41 and 46 to Enhance Cardiac Function", The Journal of General Physiology, Jun. 3, 2019, vol. 151, No. 6, pp. 758-770.
Kemp-Harper B.K., et al., "Therapeutic Potential of Nitroxyl (HNO) Donors in the Management of Acute Decompensated Heart Failure", Drugs, Sep. 2016, vol. 76, No. 14, pp. 1337-1348, 12 Pages.
Kobayashi J., et al., "Nitric Oxide Inhalation As an Interventional Rescue Therapy for COVID-19-Induced Acute Respiratory Distress Syndrome", Annals Of Intensive Care, May 20, 2020, vol. 10, No. 1, 2 Pages.
Kull F.C., et al., "Mixturs of Quaternary Ammonium Compounds and Long-chain Fatty Acids As Antifungal Agents", Applied Microbiology, Nov. 1961, vol. 9, No. 6, pp. 538-541.
Lowes B.D., et al., "Inotropes in the Beta-Blocker Era", Clinical Cardiology, Mar. 2000, vol. 23, No. 3, pp. III-11-III-16.
Ma X-L., et al., "Diminished Basal Nitric Oxide Release After Myocardial Ischemia and Reperfusion Promotes Neutrophil Adherence to Coronary Endothelium", Circulation Research, Feb. 1993, vol. 72, No. 2, pp. 403-412.
Ma X.L et al., "Opposite Effects of Nitric Oxide and Nitroxyl on Postischemic Myocardial Injury", Proceedings of the National Academy of Sciences of the United States of America, Dec. 7, 1999, vol. 96, No. 25, pp. 14617-14622.
Madjid M., et al., "Of Birds and Men: Cardiologists' Role in Influenza Pandemics", Lancet, Oct. 2004, vol. 364, No. 9442, p. 1309.
Martel J., et al., "Could Nasal Nitric Oxide Help to Mitigate the Severity of COVID-19?", Microbes and Infection, May-Jun. 2020, vol. 22, No. 4-5, pp. 168-171.
Miranda K.M., et al., "A Biochemical Rationale for the Discrete Behavior of Nitroxyl and Nitric Oxide in the Cardiovascular System", Proceedings of the National Academy of Sciences of the United States of America, Aug. 5, 2003, vol. 100, No. 16, pp. 9196-9201.
Moncada S., et al., "Nitric Oxide: Physiology, Pathophysiology, and Pharmacology", Pharmacological Reviews, Jun. 1991, vol. 43, No. 2, pp. 109-142.
Monsalve-Naharro J.A., et al., "Inhaled Nitric Oxide in Adult Patients with Acute Respiratory Distress Syndrome", Farmacia Hospitalaria, Mar. 1, 2017, vol. 41, No. 2, pp. 292-312.
Norris A.J., et al., "Nitroxyl Inhibits Breast Tumor Growth and Angiogenesis", International Journal of Cancer, Apr. 15, 2008, vol. 122, No. 8, pp. 1905-1910.
Pagliaro P., et al., "Nitroxyl Affords Thiol-Sensitive Myocardial Protective Effects Akin to Early Preconditioning", Free Radical Biology & Medicine, Jan. 1, 2003, vol. 34, No. 1, pp. 33-43.
Paolocci N., et al., "The Pharmacology of Nitroxyl (HNO) and its Therapeutic Potential: Not Just the Janus Face of NO", Pharmacology & Therapeutics, Feb. 2007, vol. 113, No. 2, pp. 442-458, 29 Pages.
Parissis J., et al., "Nitroxyl Donors for Acute Heart Failure: Promising Newcomers", European Journal of Heart Failure, Oct. 2017, vol. 19, No. 10, 1333-1334.
Porcheddu A., et al., "A Straightforward Route to Piloty's Acid Derivatives: A Class of Potential Nitroxyl-Generating Prodrugs", Synlett, 2009, No. 13, pp. 2149-2153, 6 Pages.
Qin C.X., et al., "Nitric Oxide Resistance, Induced in the Myocardium by Diabetes, Is Circumvented by the Nitric Oxide Redox Sibling, Nitroxyl", Antioxidants Redox Signaling, Jan. 1, 2020, vol. 32, No. 1, pp. 60-77, pp. 1-57.
Ricciardolo F.L.M., et al., "Nitric Oxide in Health and Disease of the Respiratory System", Physiological Reviews, Jul. 2004, vol. 84, No. 3, pp. 731-765.
Shafirovich V., et al., "Nitroxyl and its Anion in Aqueous Solutions: Spin States, Protic Equilibria, and Reactivities Toward Oxygen and Nitric Oxide", Proceedings of the National Academy of Sciences of the United States of America, May 28, 2002, vol. 99, No. 11, pp. 7340-7345.
Shoeman D.W., et al., "Reaction of Nitroxyl, An Aldehyde Dehydrogenase Inhibitor, with N-Acetyl-L-Cysteine", Alcohol, Jan. 2000, vol. 20, No. 1, pp. 55-59.
Shoman M.E., et al., "Nitroxyl (HNO): A Reduced Form of Nitric Oxide With Distinct Chemical, Pharmacological, and Therapeutic Properties," Oxidative Medicine and Cellular Longevity, 2016, 4867124, epub Dec. 7, 2015, 33 Pages.
Sidorkina O., et al., "Inhibition of Poly (ADP-Ribose) polymerase (PARP) by Nitric Oxide and Reactive Nitrogen Oxide Species", Free Radical Biology & Medicine, Dec. 1, 2003, vol. 35, No. 11, pp. 1431-1438.
Sirsalmath K., et al., "The pH of HNO Donation Is Modulated by Ring Substituents in Piloty's Acid Derivatives: Azanone Donors at Biological pH", Journal of Inorganic Biochemistry, Jan. 2013, vol. 118, pp. 134-139.
Slotwiner-Nie P.K., et al., "Infectious Diarrhea in the Elderly", Gastroenterology Clinics of North America, Sep. 2001, vol. 30, No. 3, pp. 625-635.
Smulik R., et al., "Nitroxyl (HNO) Reacts with Molecular Oxygen and Forms Peroxynitrite at Physiological pH", Biological Implications, The Journal of Biological Chemistry, vol. 289, No. 51, Dec. 19, 2014, pp. 35570-35581.
Smulik-Izydorczyk R., et al., "Decomposition of Piloty's Acid Derivatives-Toward the Understanding of Factors Controlling HNO Release", Archives of Biochemistry and Biophysics, Jan. 2019, vol. 661, pp. 132-144.

(56) References Cited

OTHER PUBLICATIONS

Stoyanovsky D.A., et al., "Effects of pH on the Cytotoxicity of Sodium Trioxodinitrate (Angeli's salt)", Journal of Medicinal Chemistry, Jan. 1, 2004, vol. 47, No. 1, pp. 210-217.

Suarez S.A., et al., "HNO Is Produced by the Reaction of NO with Thiols," Journal of the American Chemical Society, Oct. 18, 2017, vol. 139, No. 41, pp. 14483-14487, DOI: 10.1021/jacs.7b06968, ISSN: 0002-7863, XP093011312, 8 pages.

Suarez S.A., et al., "Time-Resolved Electrochemical Quantification of Azanone (HNO) at Low Nanomolar Level", Analytical Chemistry, Nov. 5, 2013, vol. 85, No. 21, pp. 10262-10269, pp. A-H.

Suarez S.A., et al., "Updating NO/HNO Interconversion Under Physiological Conditions: A Biological Implication Overview", Journal Of Inorganic Biochemistry, Mar. 2021, vol. 216, 111333, pp. 1-18.

Sun H-J., et al., "Induction of Caveolin-3/eNOS Complex by Nitroxyl (HNO) Ameliorates Diabetic Cardiomyopathy", Redox Biology, May 2020, vol. 32, No. 101493, pp. 1-15.

Sun H-J., et al., "Nitroxyl as a Potential Theranostic in the Cancer Arena", Antioxidants & Redox Signaling, Feb. 10, 2020, vol. 32, No. 5, pp. 331-349.

Sun H-J., et al., "Role of Nitroxyl (HNO) in Cardiovascular System: From Biochemistry to Pharmacology", Pharmacological Research, Sep. 2020, vol. 159, No. 104961, pp. 1-10.

Thrift A.G., et al., "Global Stroke Statistics", International Journal Of Stroke, Jan. 2017, vol. 12, No. 1, pp. 13-32, pp. 1-20.

Tita C., et al., "A Phase 2a Dose-escalation Study of the Safety, Tolerability, Pharmacokinetics and Haemodynamic Effects of BMS-986231 in Hospitalized Patients with Heart Failure with Reduced Ejection Fraction", European Journal of Heart Failure, Oct. 2017, vol. 19, No. 10, pp. 1321-1332.

Tocchetti C.G., et al., "Nitroxyl Improves Cellular Heart Function by Directly Enhancing Cardiac Sarcoplasmic Reticulum Ca2+ Cycling", Circulation Research, Jan. 5, 2007, vol. 100, No. 1, pp. 96-104.

Tocchetti C.G., et al., "Playing with Cardiac "Redox Switches": The "HNO Way" to Modulate Cardiac Function", Antioxidants & Redox Signaling, May 1, 2011, vol. 14, No. 9, pp. 1687-1698.

Tran S.L., et al., "Dr. NO and Mr. Toxic—The Versatile Role of Nitric Oxide", Biological Chemistry, Apr. 28, 2020, vol. 401, No. 5, pp. 547-572, 58 Pages.

Vaananen A.J., et al., "Cathepsin B is a Differentiation-Resistant Target for Nitroxyl (HNO) in THP-1 Monocyte/macrophages", Free Radical Biology & Medicine, Jul. 1, 2006, vol. 41, No. 1, pp. 120-131.

Velagic A., et al., "Nitroxyl: A Novel Strategy to Circumvent Diabetes Associated Impairments in Nitric Oxide Signaling", Frontiers In Pharmacology, May 19, 2020, vol. 11, No. 727, pp. 1-18.

Vetta F., et al., "Coronavirus Disease 2019 (COVID-19) and Cardiovascular Disease: A Vicious Circle", Journal Of Cardiology and Cardiovascular Research, 2020, vol. 1, No. 2, pp. 1-12.

Wang P., et al., "Recent Advances in Membrane Distillation Processes: Membrane Development, Configuration Design and Application Exploring", Journal Of Membrane Scienc, 2015, vol. 474, pp. 39-56.

Wink D.A., et al., "Orthogonal Properties of the Redox Siblings Nitroxyl and Nitric Oxide in the Cardiovascular System: a Novel Redox Paradigm", American Journal of Physiology—Heart and Circulatory Physiology, Dec. 2003, vol. 285, No. 6, pp. H2264-H2276.

Yew W-W., et al., "Does Oxidative Stress Contribute to Adverse Outcomes in HIV-Associated TB?", Journal Of Antimicrobial Chemotherapy, May 1, 2018, vol. 73, No. 5, pp. 1117-1120.

* cited by examiner

SOLID-GAS REACTION TO GENERATE NITROXYL (HNO) IN THE GAS PHASE

RELATED APPLICATION INFORMATION

This application is a national stage application under 35 U.S.C. § 371 of PCT/US2022/029572, filed May 17, 2022, which claims priority to U.S. Provisional Application No. 63/189,534 filed on May 17, 2021, the contents of which are herein incorporated by reference.

STATEMENT OF GOVERNMENTAL INTEREST

This invention was made with government support under grant CHE-1900285 awarded by the National Science Foundation. The government has certain rights in the invention.

BACKGROUND

Nitroxyl (azanone, HNO) is an inorganic small molecule that has been widely studied due to its high biological significance. Doctorovich et al., 2016; Fukuto, 2019. HNO is an expected intermediate in biochemical pathways, Doctorovich et al., 2014; Flores-Santana et al., 2011, and has reported medical applications regarding its cardioprotective action. Tocchetti et al., 2007; Guo et al., 2019; Sun et al., 2020.

This elusive, highly reactive species, as well as the related compound nitric oxide (NO), has been found to exert beneficial physiological effects, some of its own, and some overlapping those of NO. Suarez et al., 2020; Ma et al., 1999; Miranda et al., 2003. The medical use of HNO as an agent to prevent cardiac arrest, Fukuto, 2019, as a vasodilator, Velagic et al., 2020, and as an antibacterial agent, Galizia et al., 2018, is being developed by the use of HNO donors in solution.

Once formed, HNO readily reacts toward biological targets and itself, dimerizing to yield nitrous oxide ($N_2O$) and water (Scheme 1, Eqn. c). Shafirovich and Lymar, 2002. Therefore, a more controlled way to generate HNO efficiently is of interest.

SUMMARY

In some aspects, the presently disclosed subject matter provides a method for generating nitroxyl (HNO) in the gas phase, the method comprising one of:

(a) contacting a solid base-catalyzed HNO donor with a gaseous base;

(b) contacting a solid acid-catalyzed HNO donor with a gaseous acid; or (c) contacting a solid reducing agent with gaseous NO;

to form HNO in the gas phase.

In certain aspects, the gaseous base comprises ammonia ($NH_3$). In certain aspects, the method further comprises generating the ammonia ($NH_3$) by reacting ammonium hydroxide ($NH_4OH$) with sodium hydroxide.

In certain aspects, the solid base-catalyzed HNO donor comprises a Piloty's acid derivative. In particular aspects, the solid base-catalyzed HNO donor comprises a sulfohydroxamic moiety. In more particular aspects, the solid base-catalyzed HNO donor comprises a sulfohydroxamic acid. In yet more particular aspects, the solid base-catalyzed HNO donor comprises a sulfohydroxamic acid of the following formula:

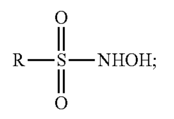

wherein R is alkyl or aryl.

In even yet more particular aspects, the Piloty's acid derivative is N-hydroxy-4-nitrobenzenesulfonamide ($NO_2$-PA) or N-hydroxy-4-fluorobenzenesulfonamide (F-PA).

In some aspects, the method further comprises one of:

(a) preparing the N-hydroxy-4-nitrobenzenesulfonamide ($NO_2$-PA) by reacting 4-methylbenzensulfonyl chloride with MgO; or (b) preparing the N-hydroxy-4-fluorobenzenesulfonamide (F-PA) by reacting hydroxylamine hydrochloride ($HCl \cdot NH_2OH$) with MgO.

In other aspects, the solid base-catalyzed HNO donor comprises 4-(N-hydroxylamino)-4-(acetyl-O-methyoxyoxime)-N-phenyl-3-methylpyrazolone (HAPY-1).

In some aspects, the solid base-catalyzed HNO donor comprises a nanoparticle or is adsorbed on a nanoparticle.

In other aspects, the solid acid-catalyzed HNO donor comprises Angeli's salt ($Na_2N_2O_3$). In certain aspects, the gaseous acid comprises HCl.

In certain aspects, the solid reducing agent comprises an alcohol or a thiol or is a reducing inorganic solid. In particular aspects, the solid reducing agent is selected from naringenin, $Ni^{+2}$-naringin, cysteine, and dithionite $(S_2O_4)^{2-}$. In another aspect, the contacting of the solid reducing agent and gaseous NO is done in the presence of one or more or $H_2O$, NaOH, $H_3PO_4$, and phosphate buffer.

In some aspects, the method further comprises monitoring the HNO in the gas phase directly or indirectly. In certain aspects, the HNO in the gas phase is monitored directly by mass spectrometry or by an electrochemical HNO sensor. In certain aspects, the HNO in the gas phase is monitored indirectly by monitoring nitrous oxide ($N_2O$) using infrared spectroscopy.

In some aspects, the method further comprises removing the gaseous acid or base from the system. In certain aspects, the method further comprises trapping the excess acid or base by using a membrane or an aqueous basic or acidic solution.

In some aspects, the method further comprises heating to minimize dimerization of the HNO to $N_2O$. In certain aspects, the method comprises heating to above 80° C. for F-PA and above 90° C. for $NO_2$-PA for about 30 minutes.

In other aspects, the presently disclosed subject matter provides a method for treating a disease or a condition responsive to nitroxyl therapy, the method comprising administering to a subject in need of treatment thereof, the HNO in the gas phase generated by the method disclosed herein.

In certain aspects, the HNO is administered via inhalation.

In certain aspects, the disease or a condition responsive to nitroxyl therapy is selected from the group consisting of a cardiovascular disease, ischemia/reperfusion injury, pulmonary hypertension (PH), cancer, alcoholism, vascular dysfunction, and a bacterial infection.

In certain aspects, the method includes reducing a need for assisted ventilation. In particular aspects, the need for assisted ventilation is induced by pneumonia or one or more other acute respiratory syndromes.

In other aspects, the presently disclosed subject matter provides a kit comprising one or more of a solid HNO donor, a solid acid-catalyzed HNO donor, a gaseous base, a gaseous acid for forming HNO in the gas phase, a solid reducing agent, and gaseous NO or components to produce gaseous NO.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
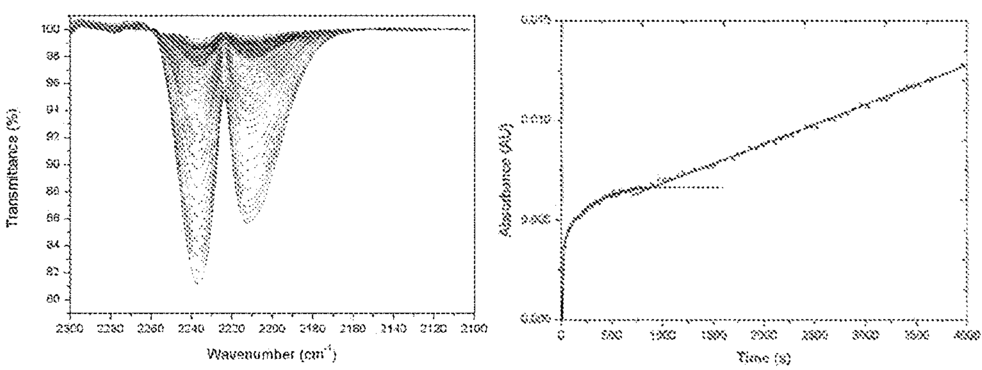
Figure 2:
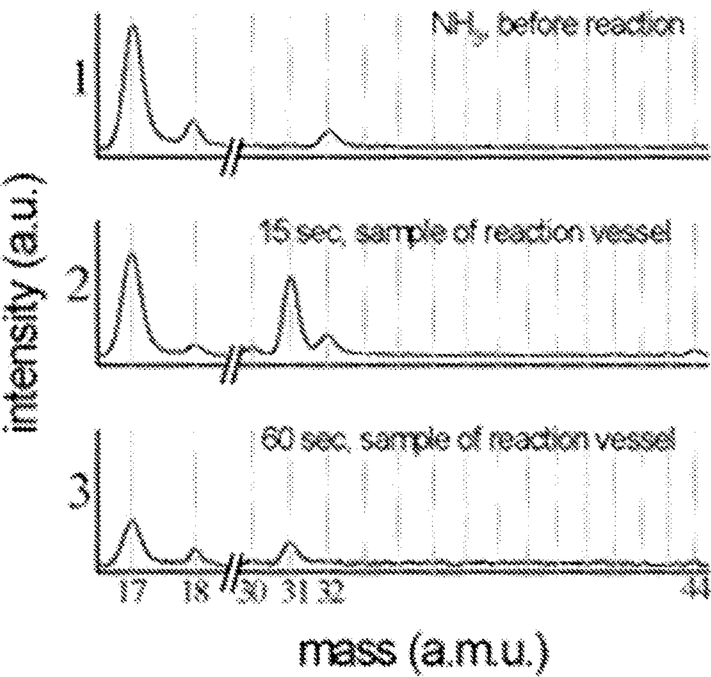
Figure 4:
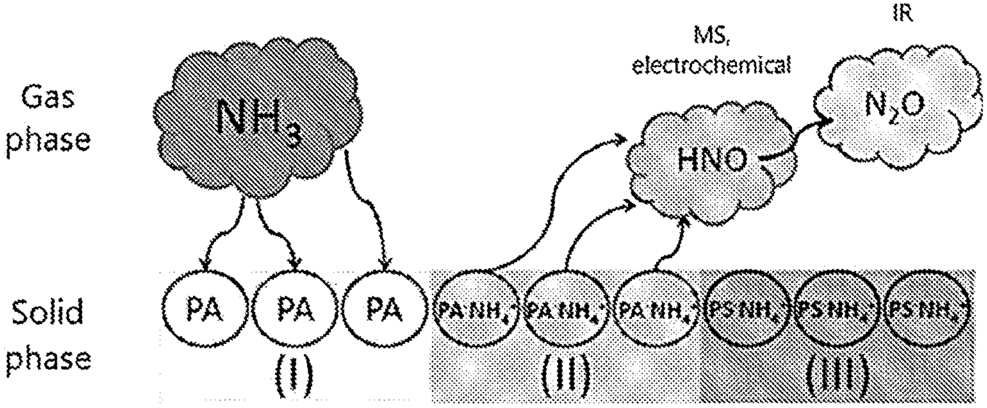
Figure 5:
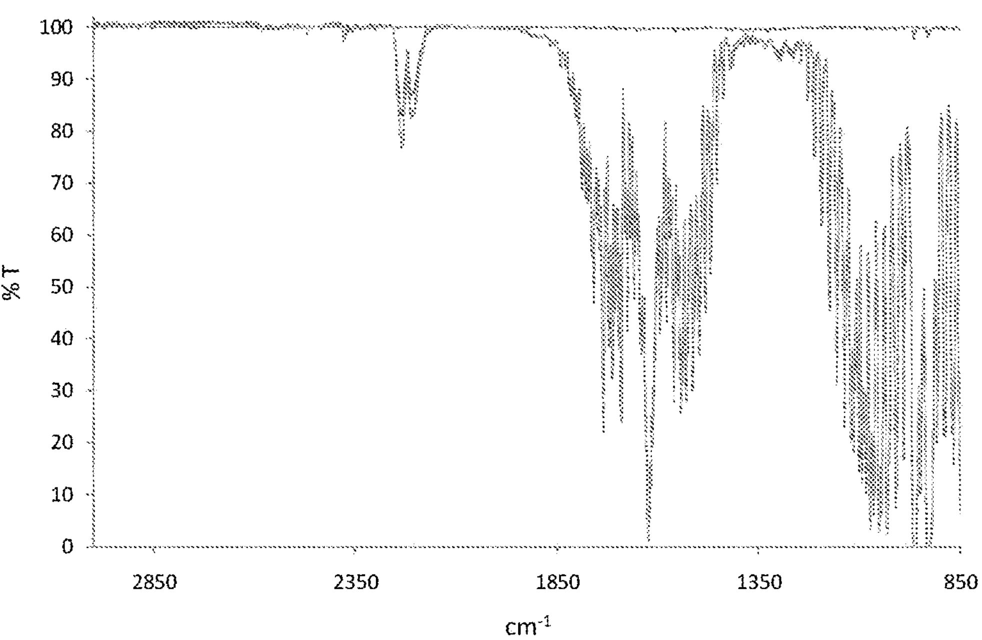
Figure 6:
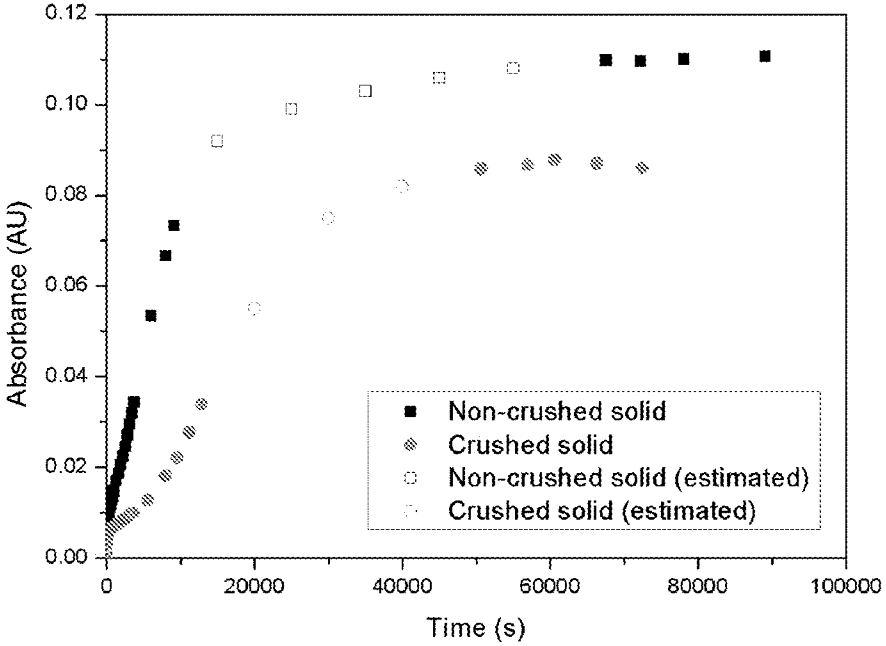
Figure 7:
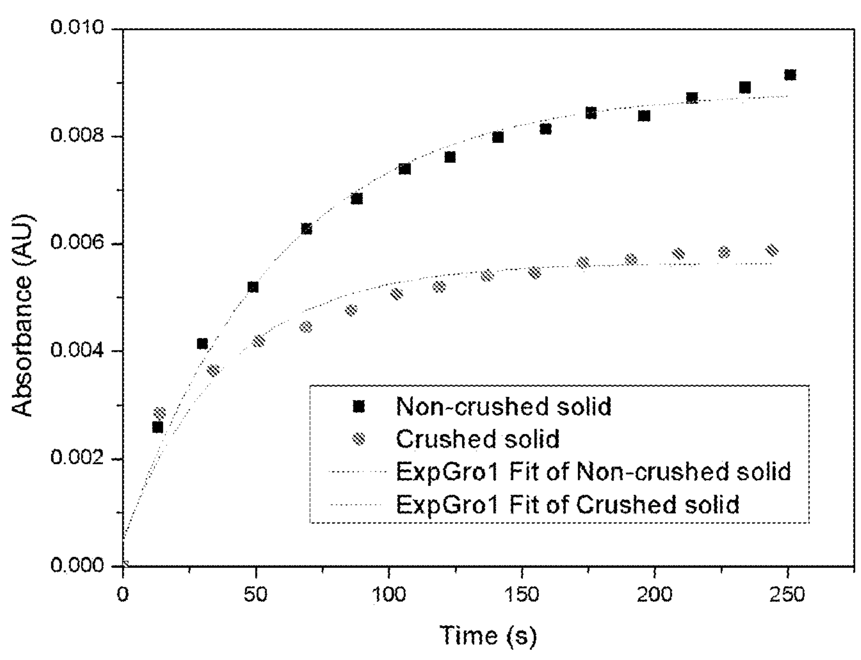
Figure 8:
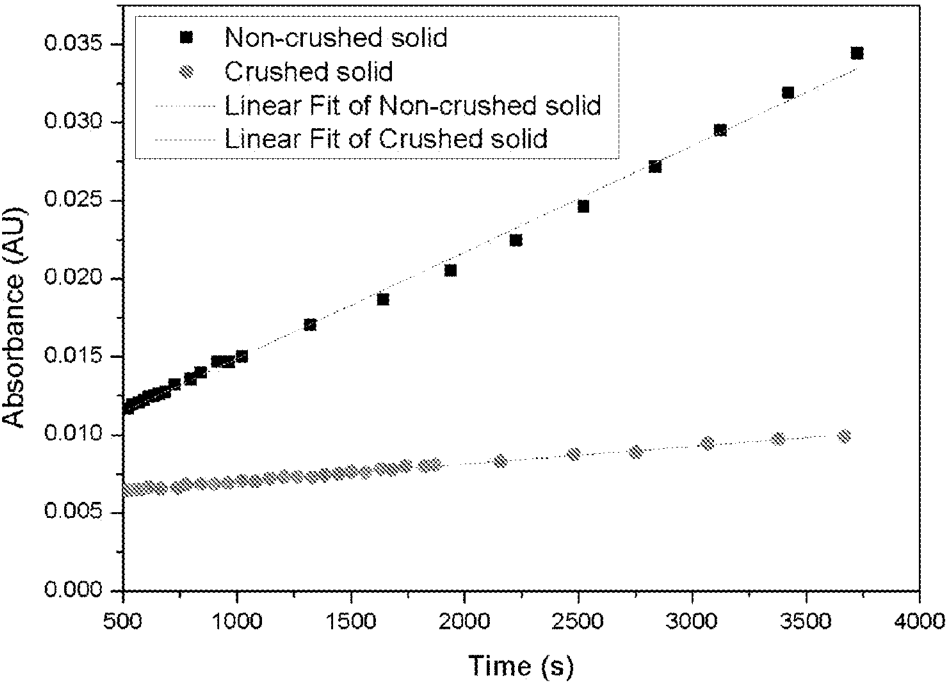
Figure 9:
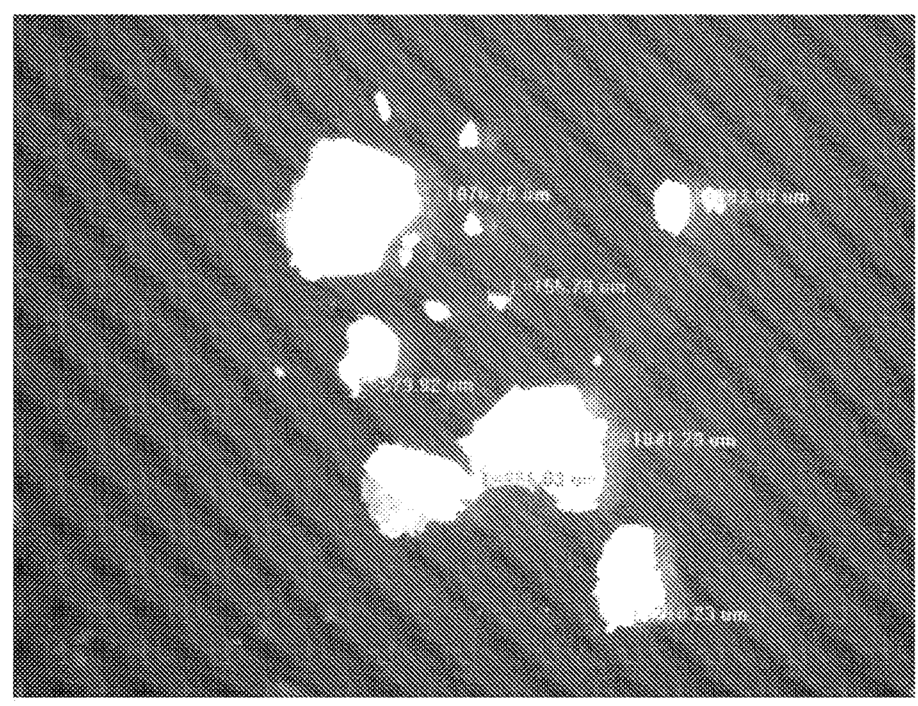
Figure 10:
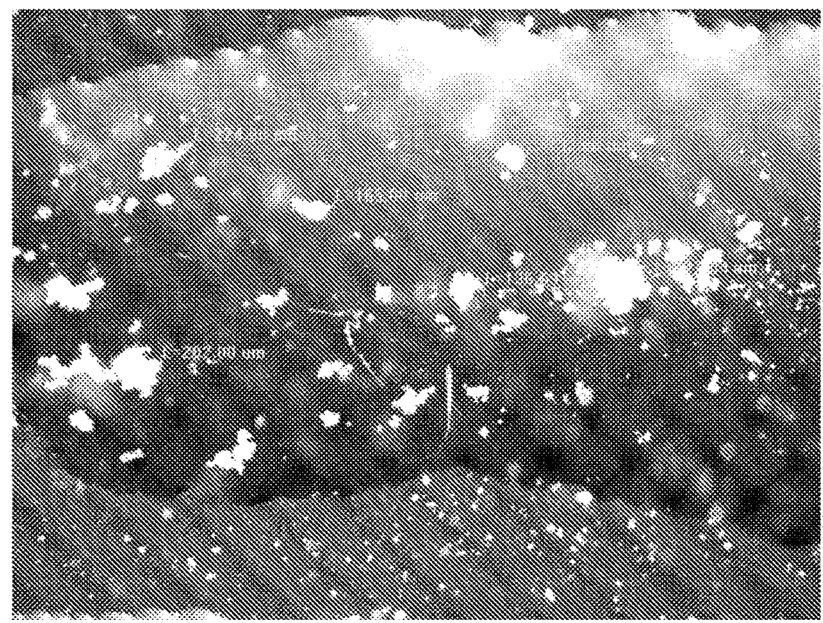
Figure 11:
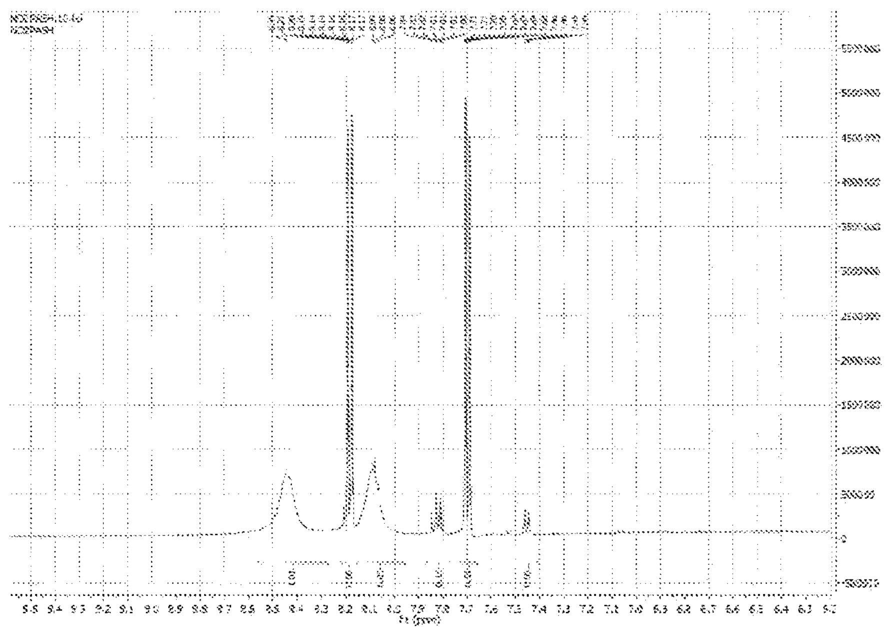
Figure 12:
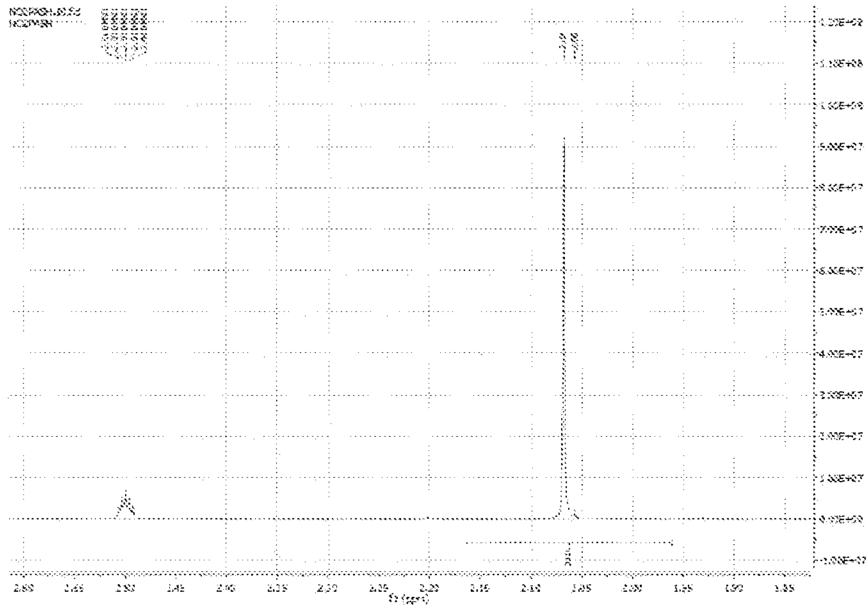

Having thus described the presently disclosed subject matter in general terms, reference will now be made to the accompanying Figures, which are not necessarily drawn to scale, and wherein:

FIG. 1A shows FT-IR spectral changes observed in the region corresponding to the characteristic $N_2O$ signal during the reaction of solid $NO_2$-PA with gaseous ammonia;

FIG. 1B shows experimental absorbance at 2237 $cm^{-1}$ ($N_2O$ signal) as a function of time, corresponding to the spectral changes observed in FIG. 1, during the first 4000 seconds. The black curves show schematically the fast growth ($k_0$, Process 1) behavior observed at short timescales followed by a linear response (Process 2, order 0, $k_{R \times N}$);

FIG. 2 shows representative mass spectra recorded along the reaction of solid $NO_2$-PA and gaseous ammonia at 90° C. Panels: (1) gaseous $NH_3$ before reaction, (2) reaction mixture at t=15 s, (3) reaction mixture at t=60 s;

FIG. 3A and FIG. 3B are mass spectra recorded from the reaction of $NO_2$-PA and anhydrous $NH_3$ (g) at RT by Procedure #2. A ratio of m/z 30 to 31 of 133:1 confirms the generation of HNO in this reaction. (FIG. 3A) $NH_3$ added at a rate of 5 mL/min and (FIG. 3B) $NH_3$ added at a rate of 2 mL/min;

FIG. 4 is a schematic representation of the mechanism of HNO formation from PA in presence of gaseous ammonia;

FIG. 5 shows the IR spectra obtained during the reaction of $NO_2$-PA (s) and $NH_3$ (g) inside the IR gas cell;

FIG. 6, FIG. 7, and FIG. 8 show the absorbance traces at 2237 $cm^{-1}$ during complete reaction with $NH_3$ for crushed and non-crushed $NO_2$-PA solid. Hollow symbols represent estimative values (not measured). Fittings and fitting parameters are shown in the Figures and Tables 2 and 3;

FIG. 9 is a photograph of the non-crushed $NO_2$-PA particles, and selected measurements;

FIG. 10 is a photograph of the $NO_2$-PA particles after crushing, and selected measurements;

FIG. 11 is an $^1H$ NMR spectrum in $d^6$-DMSO of the remaining solid after reaction of 10 mg crushed $NO_2$-PA with gaseous $NH_3$;

FIG. 12 is an internal reference signal (3 μL $CH_3CN$) integrated for the spectrum shown in FIG. 11.

Figure 13:
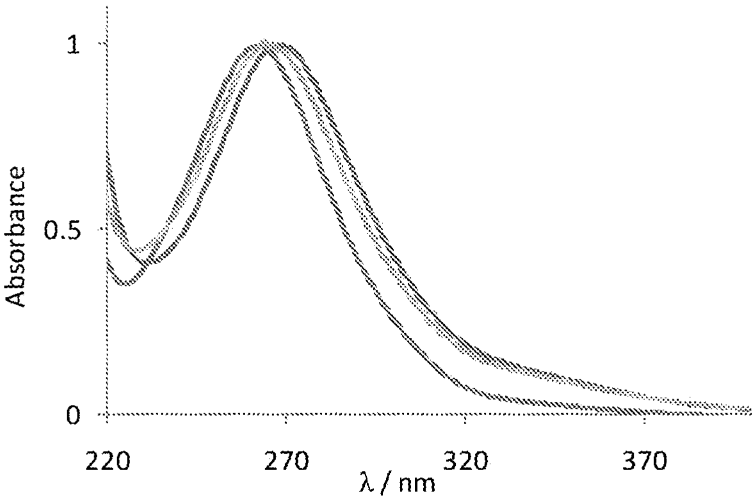
Figure 14:
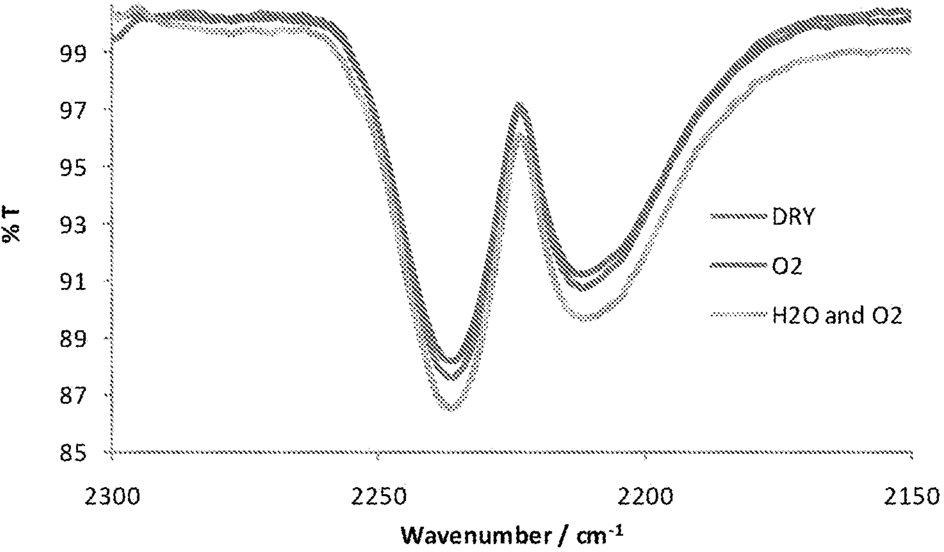
Figure 15:
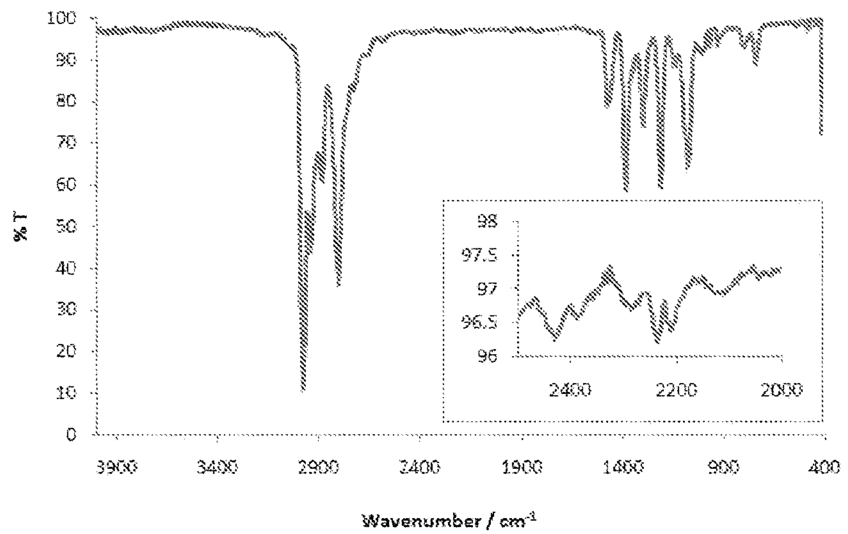
Figure 16:
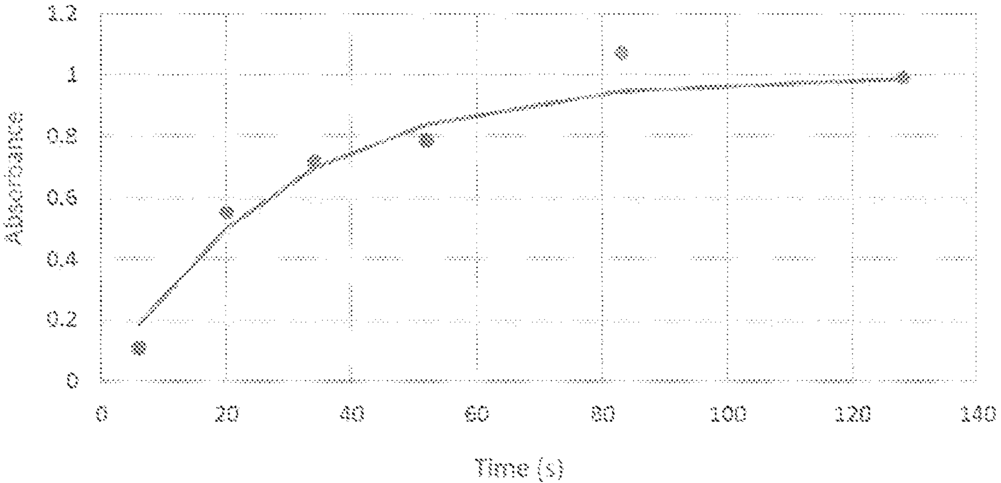
Figure 17:
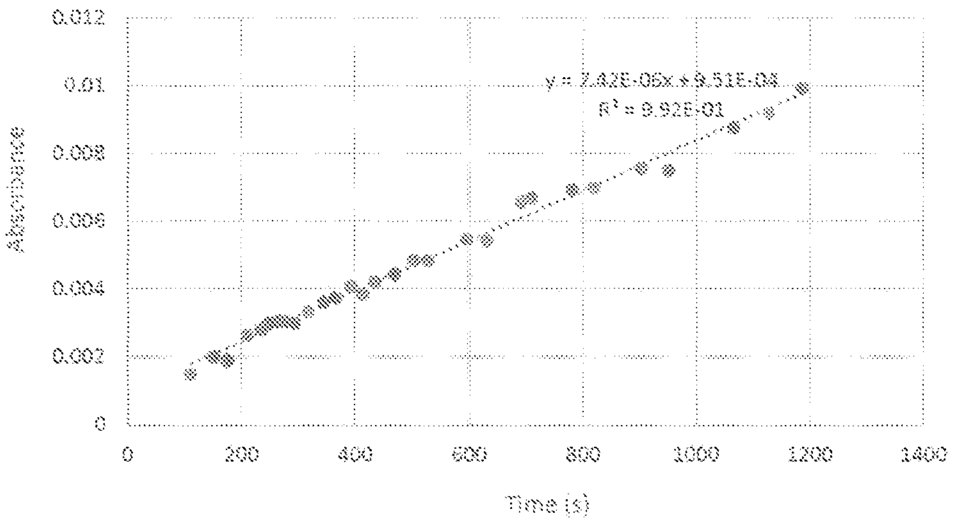
Figure 18:
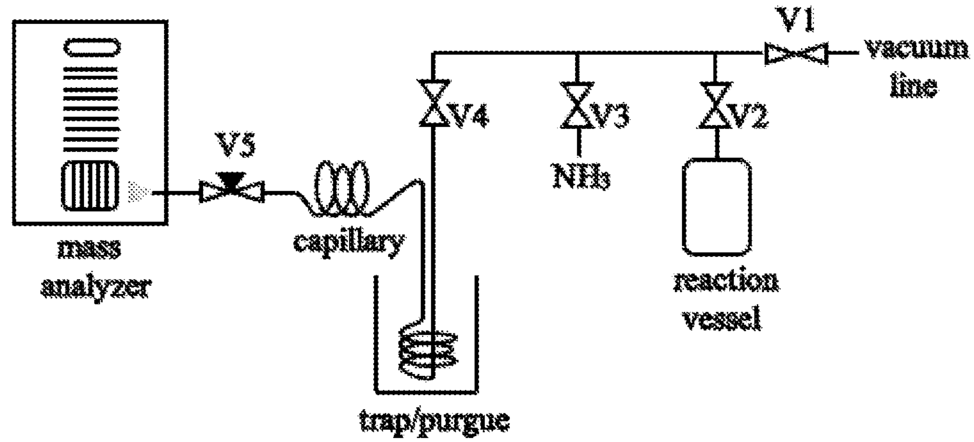
Figure 19:
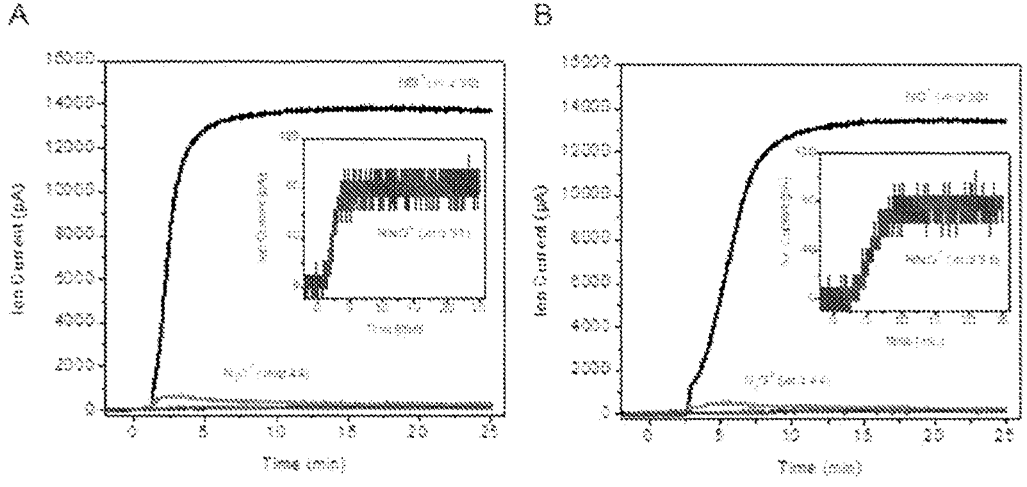
Figure 20:
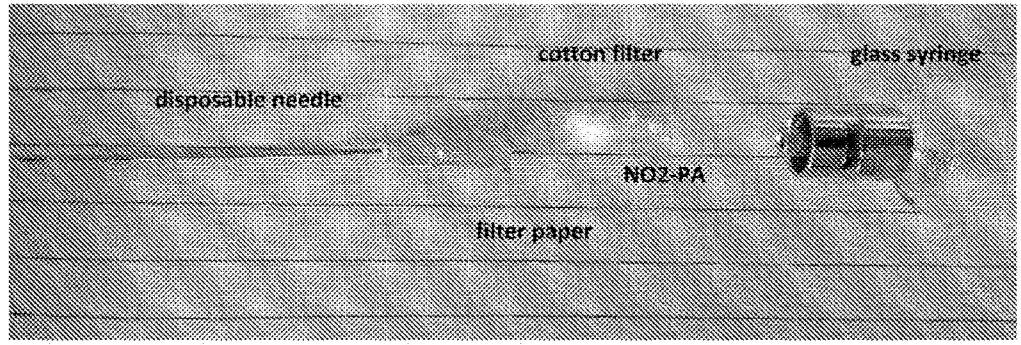
Figure 21:
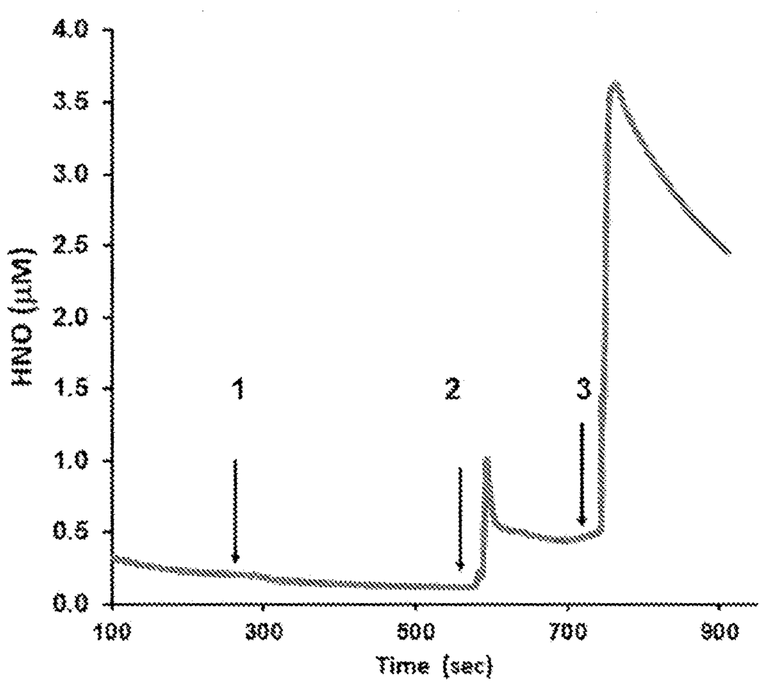
Figure 22:
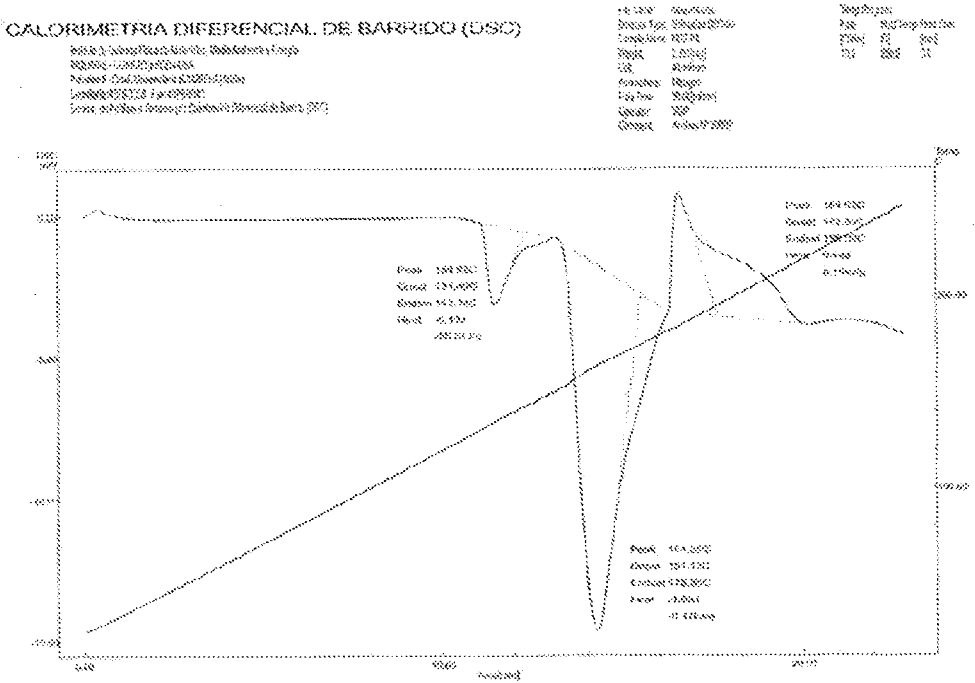
Figure 23:
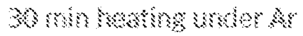
Figure 23:
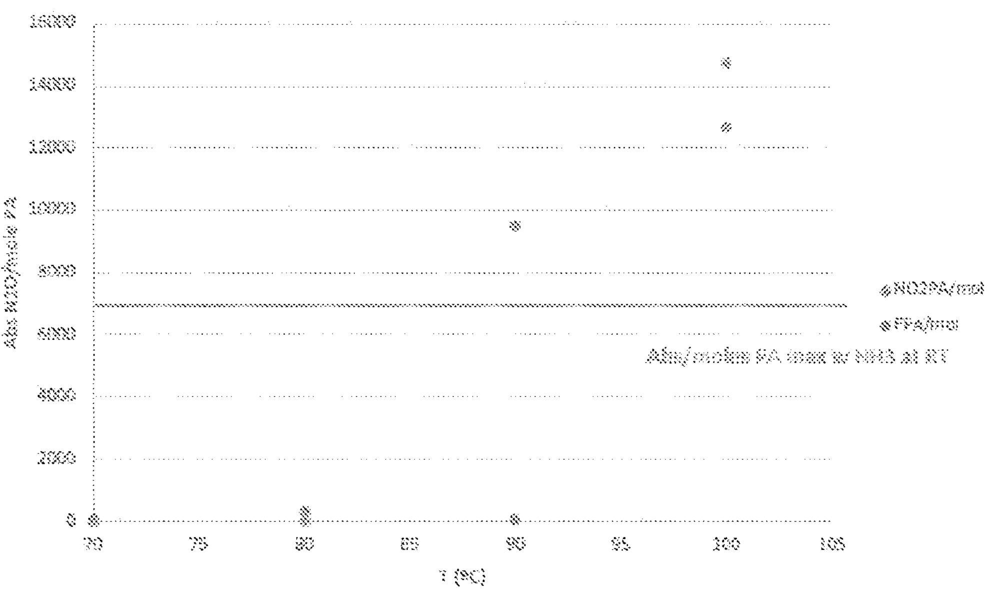
Figure 24:
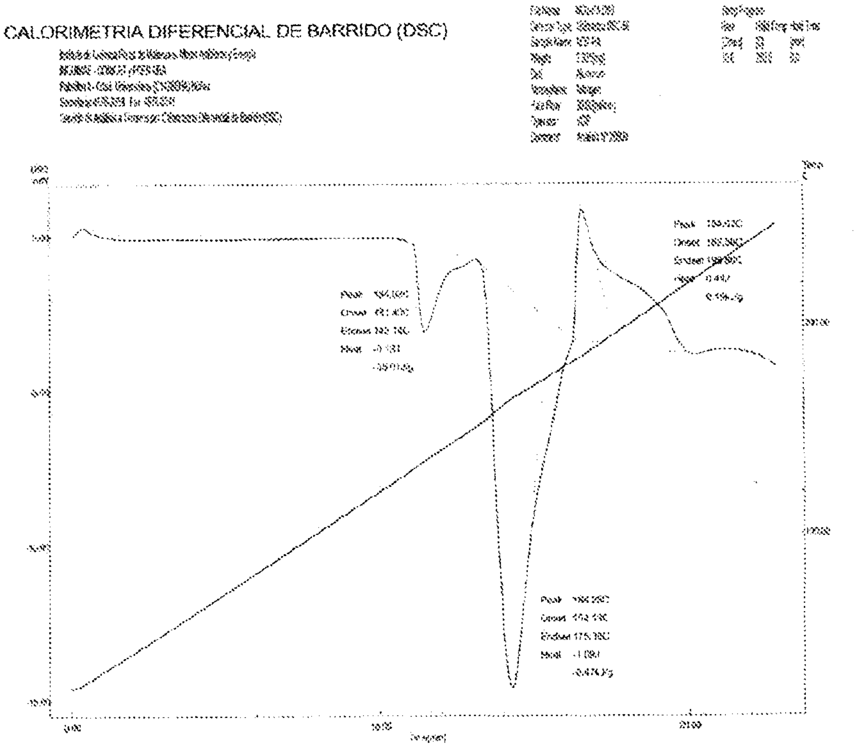
Figure 25:
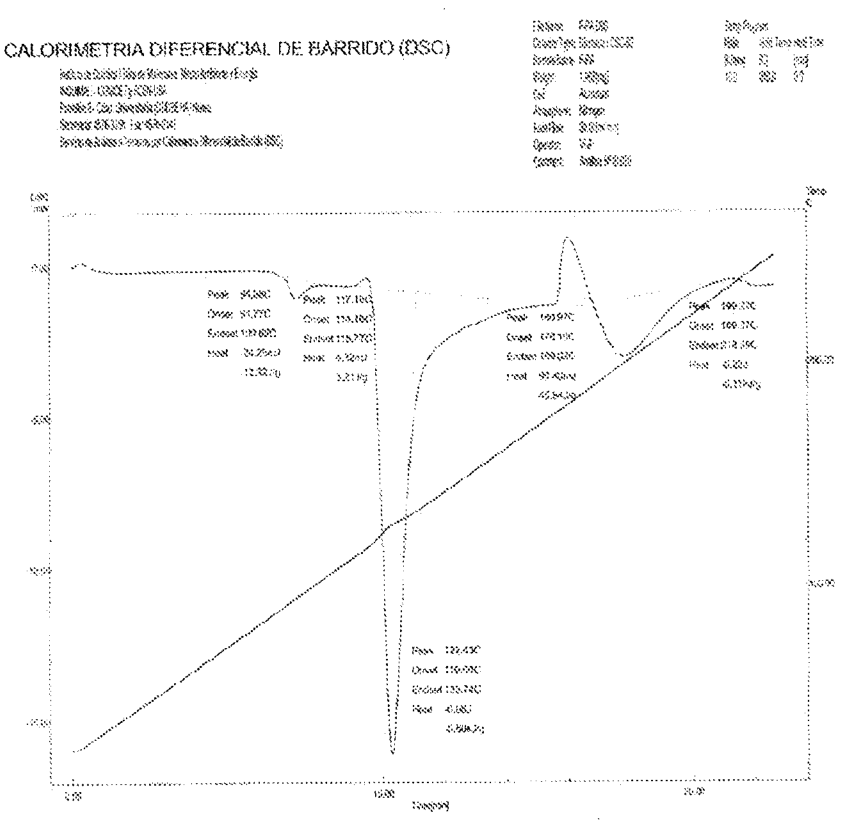
Figure 26:
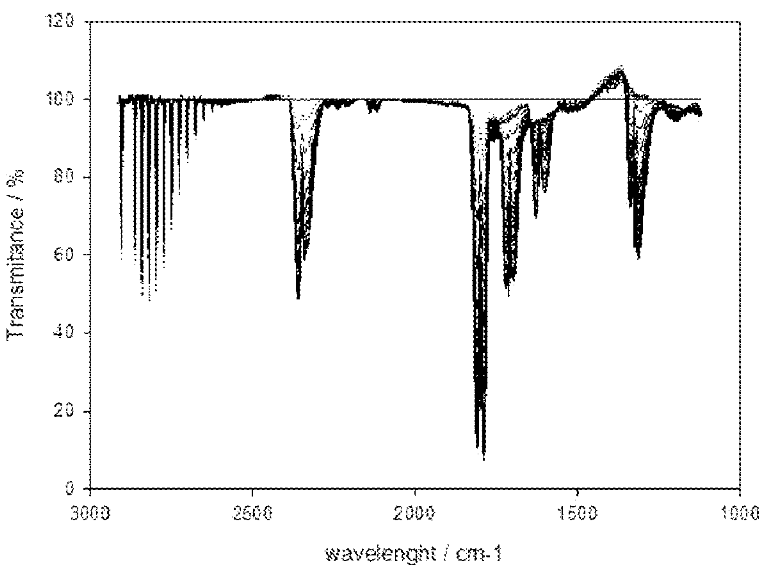
Figure 27:
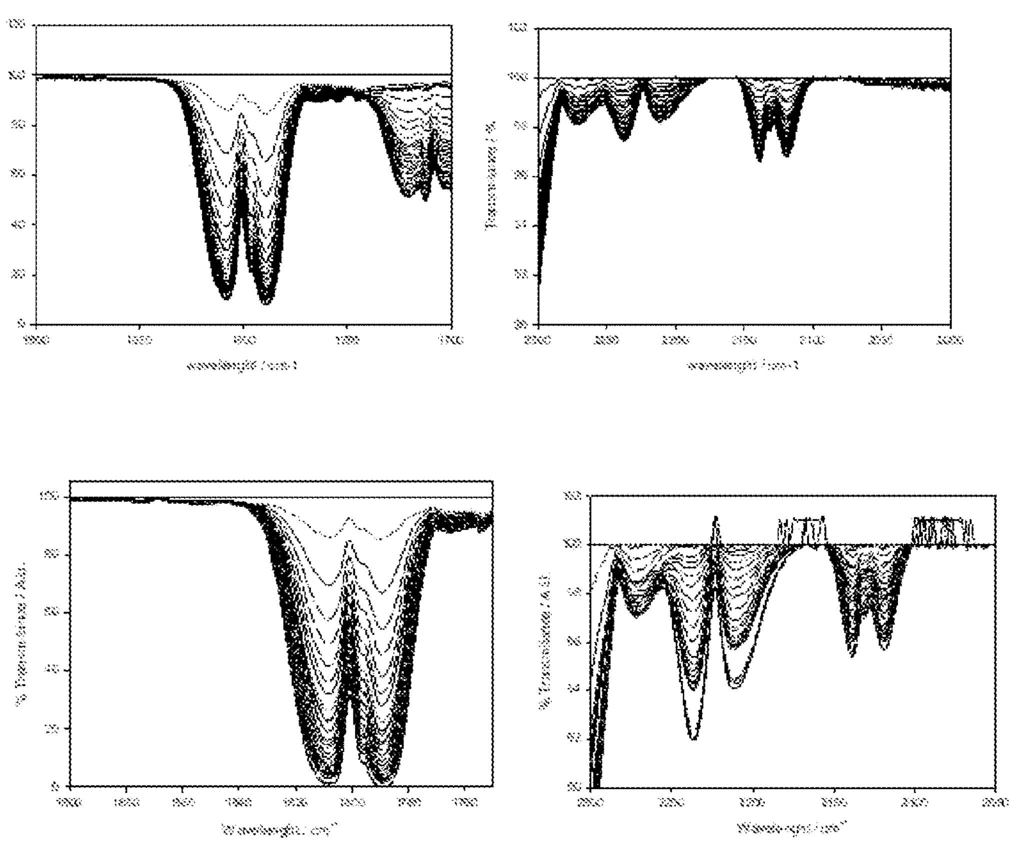
Figure 28:
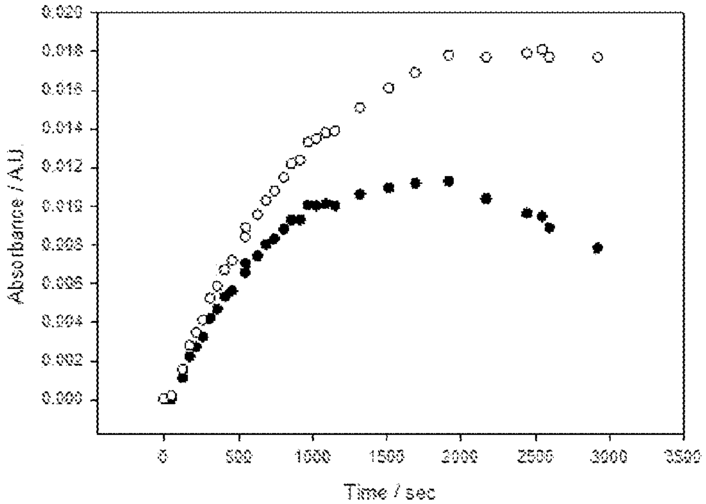
Figure 29:
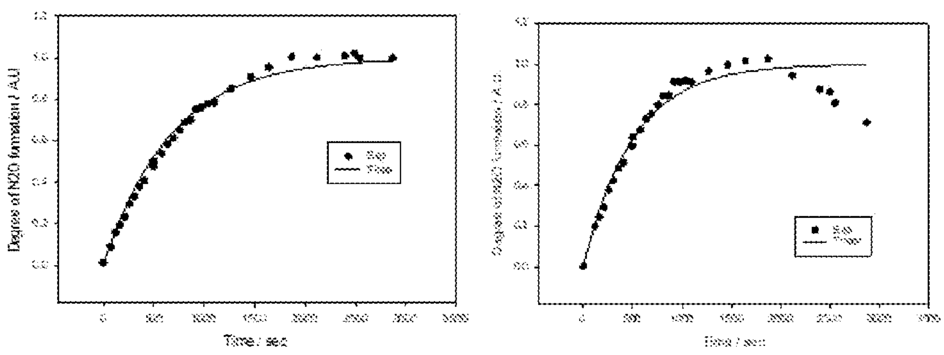
Figure 30:
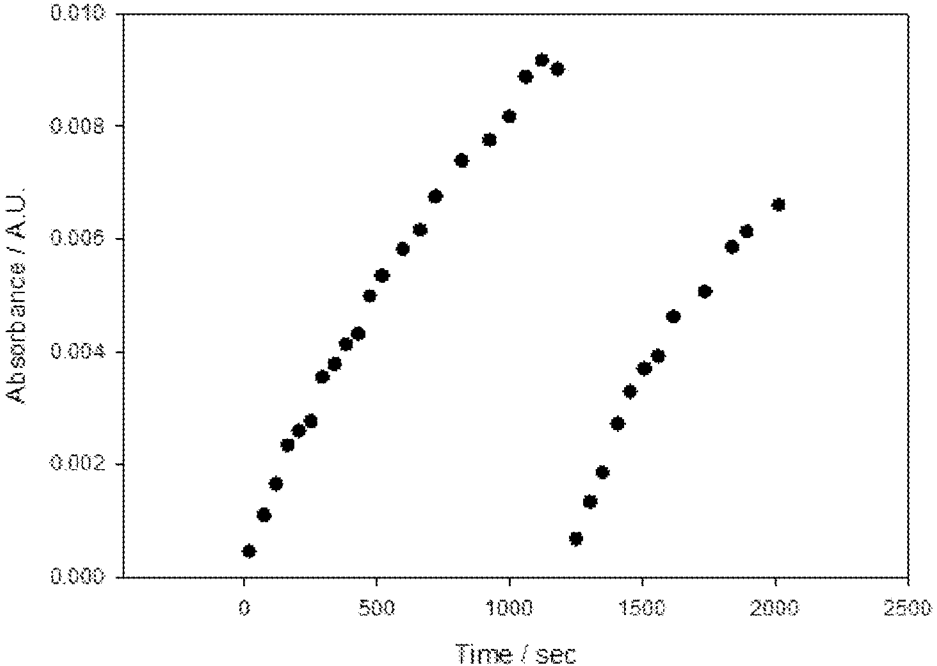
Figure 31:
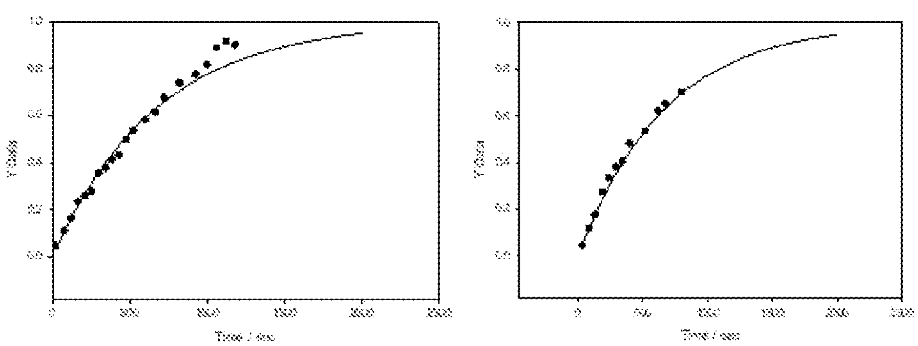
Figure 32:
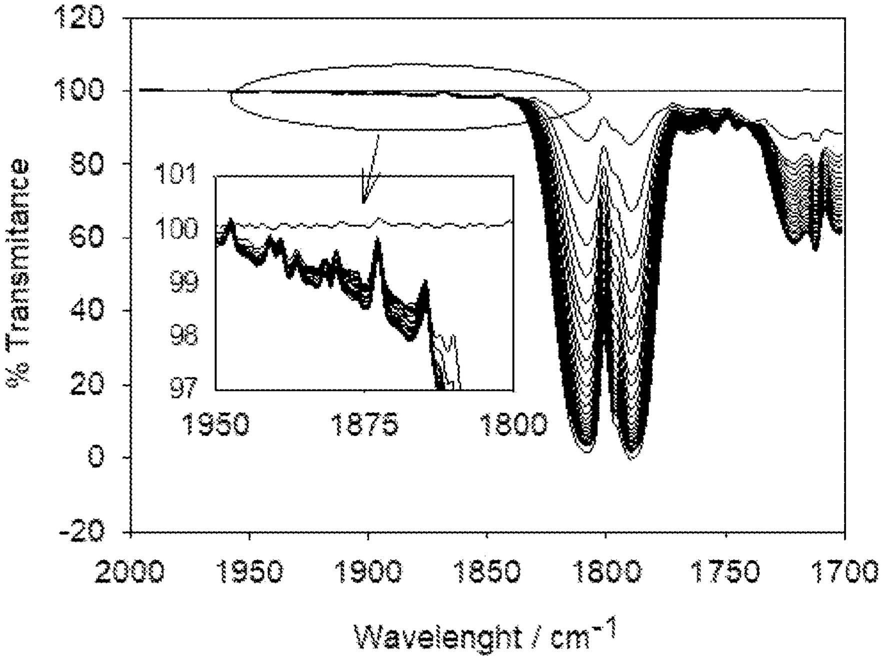
Figure 33:
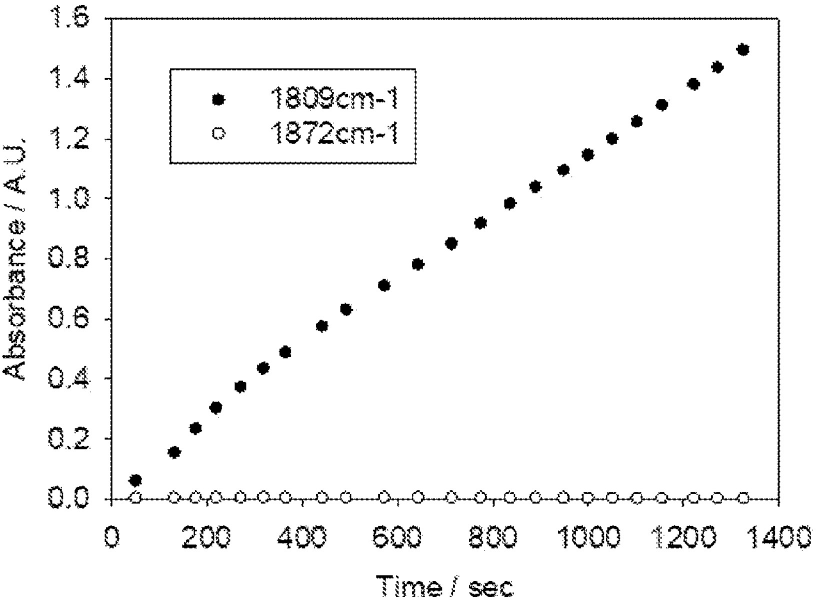
Figure 34:
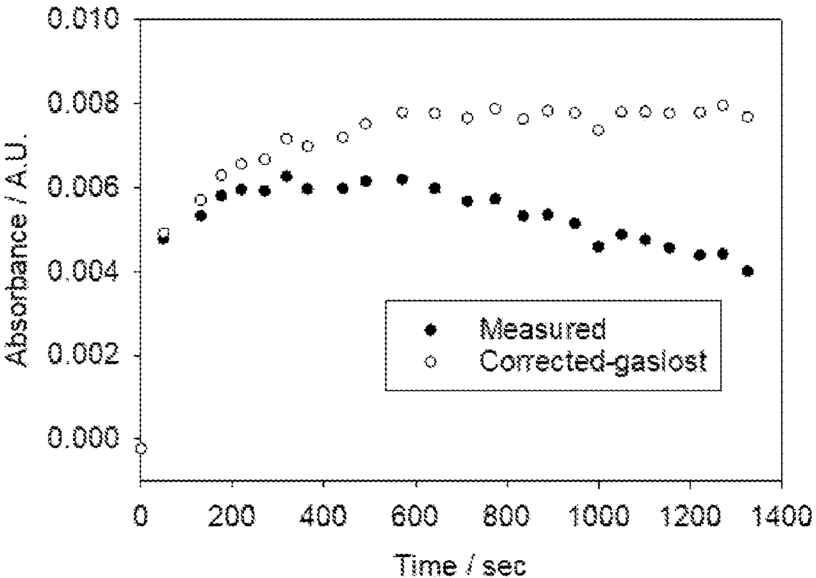
Figure 35:
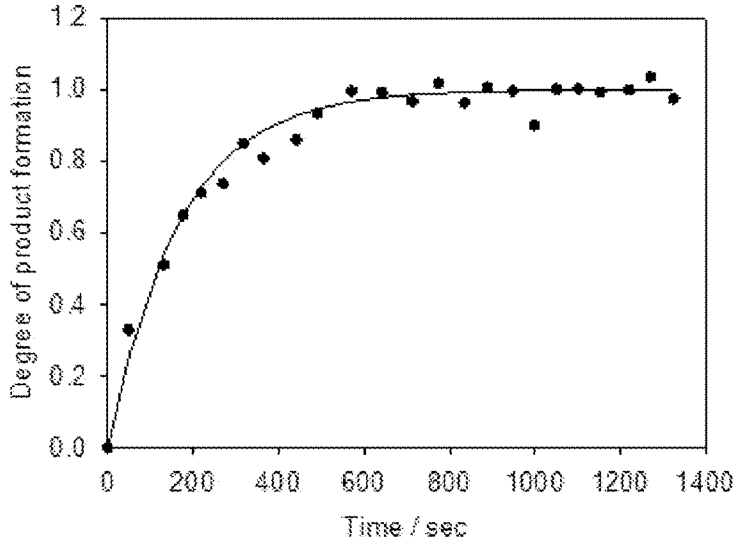
Figure 36:
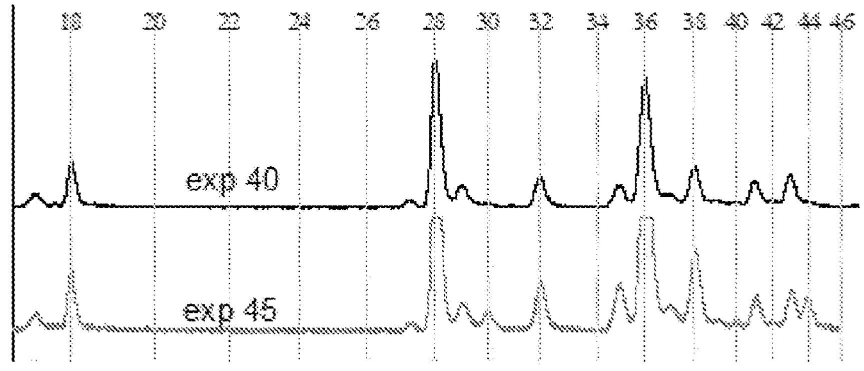
Figure 37:
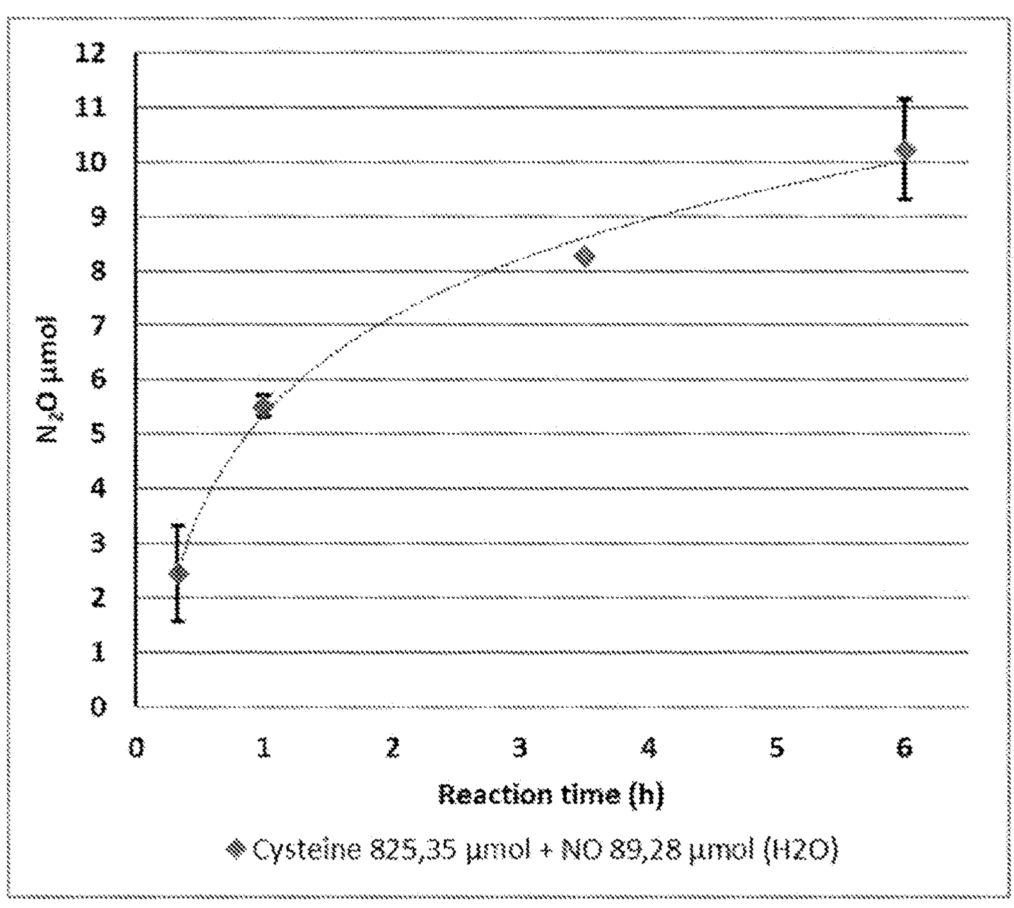
Figure 38:
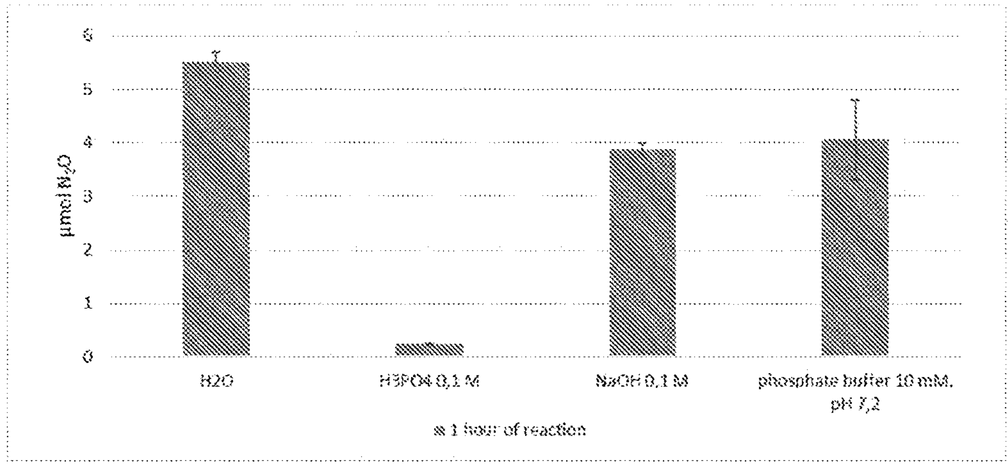
Figure 39:
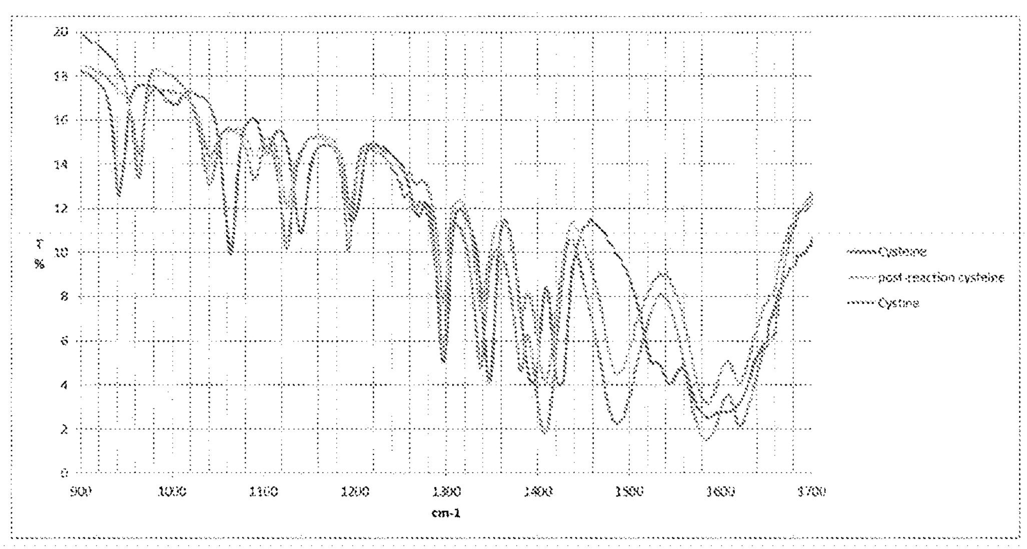
Figure 40:
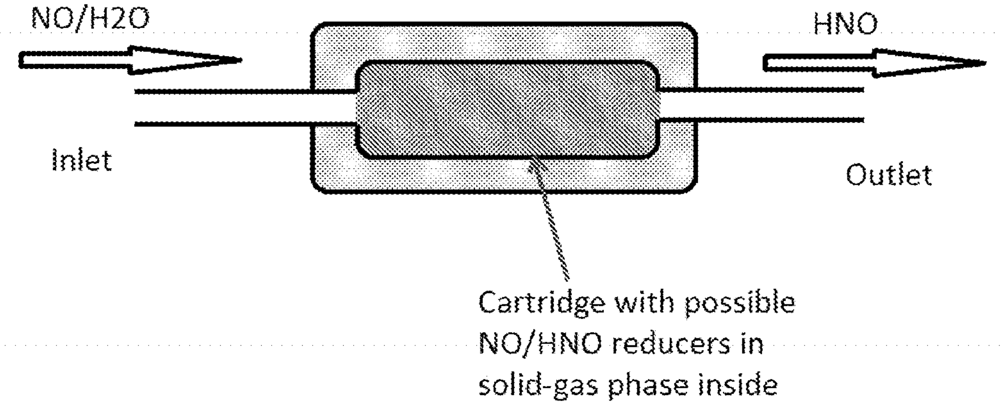

FIG. 13 shows UV-Vis spectra of $NO_2$-PA in aqueous solution before (blue) and after (red) addition of $NH_4OH$, and solid obtained of PA (s)+$NH_3$ (g), dissolved in $D_2O$ (green);

FIG. 14 is the region of IR spectra (2300-2150 $cm^{-1}$) showing $N_2O$ characteristic signal obtained by IR spectroscopy of the gas sample taken from the reaction of $NO_2$-PA (s) and $NH_3$ (g) in different experimental conditions. Dry and anaerobic atmosphere (blue), Dry and aerobic atmosphere (red), atmosphere containing $H_2O$ and $O_2$ (green);

FIG. 15 shows the IR spectra obtained after $NO_2$-PA (s) and TEA (g) reaction. Inset: Region of IR spectra showing $N_2O$ typical signal;

FIG. 16 shows the normalized absorbance changes observed at peak of $N_2O$ signal (2237 $cm^{-1}$) as a function of time shortly after adding excess $NH_3$ (g) to approximately 5 mg F-PA. Observed first order kinetic constant: k=$3.5 \times 10^{-3}$ $s^{-1}$;

FIG. 17 shows absorbance changes observed at peak of $N_2O$ signal (2237 $cm^{-1}$) at longer timescales. Observed order 0 kinetic constant: k=$1.70 \times 10^{-8}$ $M \cdot s^{-1}$;

FIG. 18 is a schematic of the manifold used to load the gaseous reactant ($NH_3$) to the reaction vessel, and interface to the mass analyzer. V1-4, isolation valves; V5, 18-turn fine metering valve;

FIG. 19 shows mass spectrum recorded from the reaction of HAPY-1 and anhydrous $NH_3$ (g) at RT by Procedure #2. A) was recorded with an $NH_3$ addition rate of 5 mL/min and B) was recorded with an $NH_3$ addition rate of 2 mL/min;

FIG. 20 shows an experimental setup used for HNO detection from solid $NO_2$PA and gaseous ammonia using a selective electrode;

FIG. 21 shows an [HNO] vs time plot after the stepwise addition of 1) argon and 2) ammonia:argon (1:10) mixture to 5 mg $NO_2$-PA, and 3) ethanol solution of $NO_2$-PA (1 mM);

FIG. 22 is a DSC plot for $NO_2$-PA;

FIG. 23 shows $N_2O$ absorbance/mole PA derivative plotted as a function of temperature;

FIG. 24 is a DSC plot showing that $NO_2$-PA starts decomposing at 131° C. and has a strong peak at 164° C. However, if heated for half an hour, as shown above, decomposition begins before 100° C.;

FIG. 25 is a DSC plot showing that F-PA starts decomposing at 92° C. and has a strong peak at 117° C. However, if heated for half an hour, as shown above, decomposition begins before 90° C.;

FIG. 26 shows IR spectra obtained during the reaction of AS (s) with HCl (g);

FIG. 27 shows the IR spectral region from 2300 to 2050 $cm^{-1}$ (right) and from 1900 to 1750 $cm^{-1}$ obtained during reaction of AS (s) with HCl (g). The signals at 2200-2250 $cm^{-1}$ are characteristic of $N_2O$, while the 2100-2150 $cm^{-1}$ and 1800 $cm^{-1}$ signals are assigned to CO and NO, respectively. The signals at ca. 1700 $cm^{-1}$ and 2275 $cm^{-1}$ remain unassigned;

FIG. 28 is the calculated absorbance at 2237 $cm^{-1}$ (black) and corrected absorbance considering the gas loss (white). Approximate $N_2O$ production yield: 2-4%;

FIG. 29 shows (Left) Degree of product formation calculated using corrected absorbance at 2237 $cm^{-1}$ (dotted) and theoretical curve (1−e^(−kt), k=$1.5 \times 10^{-3}$ $s^{-1}$); (Right) Degree of product formation calculated using absorbance at 2237 $cm^{-1}$ (dotted) and theoretical curve (1−e^(−kt), k=$2.0 \times 10^{-3}$ $s^{-1}$);

FIG. 30 is the calculated absorbance at 2237 $cm^{-1}$ (black) for two independents reactions;

FIG. 31 shows the degree of product formation (calculated using absorbance at 2237 $cm^{-1}$ (dotted) and theoretical curve (1−e^(−kt), k=$1.5 \times 10 \times^{-3}$ $s^{-1}$) for both reactions (left and right) of FIG. 30;

FIG. 32 shows the IR spectral region from 2000 to 1700 $cm^{-1}$. Inset: Region where NO signal appears;

FIG. 33 is the calculated absorbance at 1809 $cm^{-1}$ (black) and 1872 $cm^{-1}$ (white);

FIG. 34 is the calculated (black) and corrected absorbance (white) at 1872 $cm^{-1}$;

FIG. 35 shows the degree of product formation (calculated using corrected absorbance at 1872 $cm^{-1}$ (dotted) and theoretical curve (1−e^(−kt), k=$6.0 \times 10^{-3}$ $s^{-1}$;

FIG. 36 shows the HCl MS spectra (top; exp 40) where isotopic signals are present (35-37 and 36-38) and MS spectra obtained during the reaction between gaseous HCl and AS (bottom; exp 45). NO is observed at m/z 30 and $N_2O$ at m/z 44;

FIG. 37 is a graph showing $N_2O$ production versus time reaction under $H_2O$ humid conditions;

FIG. 38 shows measurements made at 1 hour of reaction under the presence of $H_2O$, 0.1 M $H_3PO_4$, 0.1 M NaOH, and 10 mM phosphate buffer pH 7;

FIG. 39 shows the FTIR spectra of cysteine, cystine, and product of reductant:NO reaction; and FIG. 40 is a scheme of a representative HNO production device for the reduction of NO in the solid-gas phase.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figure. Therefore, it is to be understood that the presently disclosed subject matter is not to be limited to the specific embodiments disclosed and that modifications and other embodiments are intended to be included within the scope of the appended claims.

A. Method for Generating Nitroxyl (HNO) in the Gas Phase

In some embodiments, the presently disclosed subject matter provides a method for generating nitroxyl (HNO) in the gas phase, the method comprising one of:

(a) contacting a solid base-catalyzed HNO donor with a gaseous base;

(b) contacting a solid acid-catalyzed HNO donor with a gaseous acid; or (c) contacting a solid reducing agent with gaseous NO;

to form HNO in the gas phase.

In certain embodiments, the gaseous base comprises ammonia ($NH_3$). In certain embodiments, the method further comprises generating the ammonia ($NH_3$) by reacting ammonium hydroxide ($NH_4OH$) with sodium hydroxide.

In certain embodiments, the solid base-catalyzed HNO donor comprises a Piloty's acid derivative. In particular embodiments, the solid base-catalyzed HNO donor comprises a sulfohydroxamic moiety. In more particular embodiments, the solid base-catalyzed HNO donor comprises a sulfohydroxamic acid. In yet more particular embodiments, the solid base-catalyzed HNO donor comprises a sulfohydroxamic acid of the following formula:

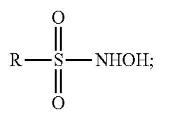

wherein R is alkyl or aryl.

As used herein, the term "alkyl," by itself or as part of another substituent, means, unless otherwise stated, a straight (i.e., unbranched) or branched chain acyclic hydrocarbon having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons. Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below.

In even yet more particular embodiments, the Piloty's acid derivative is N-hydroxy-4-nitrobenzenesulfonamide ($NO_2$-PA) or N-hydroxy-4-fluorobenzenesulfonamide (F-PA).

In some embodiments, the method further comprises one of.

(a) preparing the N-hydroxy-4-nitrobenzenesulfonamide ($NO_2$-PA) by reacting 4-methylbenzensulfonyl chloride with MgO; or (b) preparing the N-hydroxy-4-fluorobenzenesulfonamide (F-PA) by reacting hydroxylamine hydrochloride ($HCl\cdot NH_2OH$) with MgO.

In other embodiments, the solid base-catalyzed HNO donor comprises 4-(N-hydroxylamino)-4-(acetyl-O-methyoxyoxime)-N-phenyl-3-methylpyrazolone (HAPY-1).

In some embodiments, the solid base-catalyzed HNO donor comprises a nanoparticle or is adsorbed on a nanoparticle.

In other embodiments, the solid acid-catalyzed HNO donor comprises Angeli's salt ($Na_2N_2O_3$). In certain embodiments, the gaseous acid comprises HCl.

In certain embodiments, the solid reducing agent comprises an alcohol or a thiol or is a reducing inorganic solid. In particular embodiments, the solid reducing agent is selected from naringenin, $Ni^{+2}$-naringin, cysteine, and dithionite $(S_2O_4)^{2-}$. In another embodiment, the contacting of the solid reducing agent and gaseous NO is done in the presence of one or more or $H_2O$, NaOH, $H_3PO_4$, and phosphate buffer.

In some embodiments, the method further comprises monitoring the HNO in the gas phase directly or indirectly. In certain embodiments, the HNO in the gas phase is monitored directly by mass spectrometry or by an electrochemical HNO sensor. In certain embodiments, the HNO in the gas phase is monitored indirectly by monitoring nitrous oxide ($N_2O$) using infrared spectroscopy.

In some embodiments, the method further comprises removing the gaseous acid or base from the system. In certain embodiments, the method further comprises trapping the excess acid or base by using a membrane or an aqueous basic or acidic solution.

In some embodiments, the method further comprises heating to minimize dimerization of the HNO to $N_2O$. In certain embodiments, the method comprises heating to above 80° C. for F-PA and above 90° C. for $NO_2$-PA for about 30 minutes.

In other embodiments, the presently disclosed subject matter provides a kit comprising one or more of a solid HNO donor, a solid acid-catalyzed HNO donor, a gaseous base, a gaseous acid for forming HNO in the gas phase, a solid reducing agent, and gaseous NO or components to produce gaseous NO.

B. Methods for Treating a Disease or Condition Responsive to Nitroxyl Therapy

In some embodiments, the presently disclosed subject matter provides a method for treating a disease or condition responsive to nitroxyl therapy. In certain embodiments, the presently disclosed methods increase in vivo nitroxyl levels by administering to a subject in need of treatment HNO in the gas phase as generated by the methods disclosed herein. In various embodiments, the subject has, is suspected of having, or is at risk of having or developing a condition that is responsive to nitroxyl therapy.

As used herein, a condition that is "responsive to nitroxyl therapy" includes any condition in which administration of HNO in the gas phase under physiological conditions treats and/or prevents the condition, as those terms are defined herein. A condition whose symptoms are suppressed or diminished upon administration of HNO in the gas phase is a condition responsive to nitroxyl therapy.

In particular embodiments, the presently disclosed subject matter provides a method for treating, preventing or delaying the onset and/or development of a condition responsive to nitroxyl therapy, the method comprising administering to a subject (including a subject identified as in need of such treatment, prevention or delay) an effective amount of HNO in the gas phase as disclosed herein. Identifying a subject in need thereof can be in the judgment of a physician, clinical staff, emergency response personnel or other health care professional and can be subjective (e.g., opinion) or objective (e.g., measurable by a test or diagnostic method).

In certain embodiments, the HNO is administered via inhalation.

Particular diseases or conditions embraced by the methods disclosed herein include, without limitation, one or more cardiovascular diseases, including heart failure, ischemia/reperfusion injury, pulmonary hypertension (PH), cancer, alcoholism, vascular dysfunction, and a bacterial infection.

Nitric oxide and nitroxyl mainly have pharmacological effects related to the cardiovascular system, Moncada et al., 1991; Paolocci et al., 2007, although they also have anticancer properties, Sun et al., 2020; Shoman et al., 2016; Basudhar et al., 2016, also against diabetes, Velagic et al., 2020; Qin et al., and respiratory illness. Ricciardolo et al., Galizia et al., 2018. See also, Suhrez et al., 2021, for a detailed discussion on the pharmacological effects of HNO.

Briefly, myocardial infarction and cerebral stroke are pathologies that are characterized by the death of a portion of the heart muscle that occurs when a coronary artery is completely blocked, or the brain cells, causing permanent damage. Both events make up the main causes of death from non-communicable diseases in the world. Feigin et al., 2016; Thrift et al., 2017. NO· regulates blood flow by transmitting the relaxation signal from the endothelium (where NO· is produced) to the NO· responsive vascular smooth muscle cells. Fukuto et al., 1994; Vaananen et al., 2006. Over the past 20 years, however, HNO donors have been shown to produce different in vivo effects than those observed for NO·. Adak et al., 2000; Sidorkina et al., 2003; Ma et al., 1999; Wink et al., 2003. Moreover, it is suggested that some of the protective effects assigned to NO· may actually be mediated by azanone. Chouchani et al., 2013.

Specifically, HNO is linked to the protection of the cardiovascular system in the prevention of ischemia, heart attacks, and cerebral strokes (a property that NO-donors do not possess). Paolocci et al., 2007. Nitroxyl acts, mainly, in (1) the increase of muscular contractility, (2) the acceleration of the ventricular relaxation, and (3) the decrease in the cardiac output. Tocchetti et al., 2007; Guo et al., 2019; Tocchetti et al., 2011; Hartman et al., 2018; Keceli et al., 2019; Sun et al., 2020.

HNO donors cause an increase in the contractility of the heart muscle through a combined positive effect of force related to muscle contraction. This, together with the simultaneous relaxation of the cardiac muscles (inotropic and lusitropic effects, respectively), results in an increase and protection of cardiac function. Hartman et al., 2018.

Moreover, with the recent development of synthetic, next-generation nitroxyl (HNO) donors and their progress into clinical trials, Parissis et al., 2017; Tita et al., 2017, it is timely to now provide an update on the therapeutic potential of HNO donors in the management of acute decompensated heart failure. Kemp-Harper et al., 2016.

Another therapeutic application in the cardiovascular system of HNO is due to the fact that it can be a powerful preconditioning agent, which helps to alleviate the negative consequences of an ischemic event and the consequent reperfusion injury. Ma et al., 1993. This injury is characterized by deprivation of blood flow followed by necrosis and possible hypoxia of the heart tissue. Animal studies show that a dramatic decrease in infarct size was achieved by pretreating heart tissue with Angeli's salt (an HNO donor). HNO, however, also has been shown to increase infarct size if administered during an ischemic event. Pagliaro, et al., 2003. In this case, the pharmacological effect of NO· is again drastically different, since it has protective properties in reperfusion injuries of cardiac ischemia when administered during the reperfusion phase. Ma et al., 1999.

On the other hand, NO· maintains normal cardiovascular function by activating the soluble guanylate cyclase signaling pathway, Arnold et al., 1977, as well, the role of nitric oxide in the development and progression of cancers are properly established. Hirst et al., 2010; Kashfi, 2020. Similar to NO·, the pro-oxidant and antioxidant effects of HNO have been observed, becoming an effective anticancer agent. Nitroxyl donors have been revealed to restrain the proliferation of breast cancer cells, Norris et al., 2007, trigger cancer cell apoptosis, retard tumor angiogenesis, Norris et al., 2007, and reduce tumor growth. Stoyanovsky et al., 2004. Regarding the mechanism, HNO irreversibly hinders the activity of glyceraldehyde 3-phosphate dehydrogenase (GAPDH), a critical enzyme in glycolysis, that most solid tumors use as their main source of energy. As well known that HNO can interact with specific thiol proteins that modulate fundamental cellular functions, Fukuto and Carrington, 2011, then, nitroxyl reacts with cysteine thiolate within the enzyme aldehyde dehydrogenase, resulting in inhibition of this enzyme. DeMaster et al., 1998; Shoeman et al., 2000.

Furthermore, HNO donors may serve as adjuvant agents for cancer chemotherapy. Recent studies show that breast cancer cells are affected by the presence of nitroxyl through their interaction with the poly (ADPRibose) polymerase inhibitor (PARP). The role of PARP is considered critical in the DNA repair process, and therefore the ability to inhibit PARP can potentially provide an effective approach to disrupting cancer cell reproduction. Geethakumari et al., 2017; D'Andrea, 2018. Although HNO donors possess the therapeutic potential to prevent different cancers, the biochemical activities of nitroxyl in the cancer system, however, have still been incompletely understood. Sun et al., 2020.

Because of cardiovascular complications, diabetes is associated with an increased risk of mortality. Oxidative stress induced by hyperglycemia underlies these complications, leading to a deterioration in endogenous nitric oxide generation, along with reductions in the bioavailability of NO· and the responsiveness of it in the vasculature, platelets, and the myocardium. Thus, resistance to NO· (impaired responsiveness) compromises the ability of traditional nitric oxide-based therapies to improve hemodynamic status during cardiovascular emergencies associated with diabetes, as for example acute myocardial infarction. Velagic et al., 2020; Qin et al., 2020.

In 2020, Ritchie and Kemp-Harper's lab demonstrates for the first time that diabetes impairs NO·-induced left ventricular inotropic and lusitropic responses in isolated hearts, thus constituting the first definitive observation that NO· resistance occurs within the myocardium. This is followed by impaired NO·-induced dilation in the mesenteric and coronary vasculature. In contrast, vasodilator responses to an HNO donor were intact, while positive inotropic and lusitropic responses were enhanced. Velagic et al., 2020; Qin et al., 2020. In summary, HNO donors would facilitate a new therapeutic approach to treat diabetes-associated cardiovascular complications. Sun et al., 2020.

Regarding respiratory illness, several studies have been conducted to assess the relationship between levels of exhaled NO· and parameters of lung function or other markers of airway inflammation. Ricciardolo et al., 2004. Moreover, recently, as reactive oxygen and nitrogen species (RONS) are key compounds used by the immune system to fight intracellular infections, it was identified that the presence of RONS is related with *Mycobacterium tuberculosis*' (Mtb) redox status. Yew et al., 2018; Galizia and Marti, 2018. For example, NO· has been reported to inhibit the growth of or kill a number of fungi, parasites, and bacteria including *Mycobacterium tuberculosis*. Denis, 1991; Jamaati et al., 2017.

Further, in 2018, Marti et. al. show that HNO donors can affect Mtb growth. Regarding a possible mechanism of action, the authors propose that HNO acts by interfering with the general mycobacterial physiological state. Galizia et al., 2018. The question of whether RONS presence is positive or negative in the context of Tuberculosis treatment, however, is still a matter of intense debate and research. Galizia et al., 2018; Jamaati et al., 2017; Porrini et al., 2020.

Finally, it is known that pre-existing cardiovascular diseases are widely represented in patients with severe acute respiratory infections and are associated with poorer prognosis. Madjid and Casscells, 2004. Coronavirus Disease 2019 (COVID-19), has also shown a specific tropism towards the cardiovascular system, showing itself responsible for a series of severe acute and chronic diseases. Vetta et al., 2019. In this way, recent studies suggest that therapies designed to increase airway NO· levels via gas inhalation and donor molecules may improve oxygenation and produce health benefits in COVID-19 subjects. Kobayashi and Murata, 2020; Martel et al., 2020.

1. Cardiovascular Diseases

In one embodiment, the presently disclosed subject matter provides a method for treating one or more cardiovascular diseases. Representative cardiovascular diseases include, but are not limited to, coronary obstructions, coronary artery disease (CAD), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

2. Heart Failure

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

Several types of CHF exist. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. Often, an individual experiencing heart failure will have some degree of both systolic heart failure and diastolic heart failure.

CHF also can be classified according to its severity. The New York Heart Association classifies CHF into four classes: Class I involves no obvious symptoms, with no limitations on physical activity; Class II involves some symptoms during or after normal activity, with mild physical activity limitations; Class III involves symptoms with less than ordinary activity, with moderate to significant physical activity limitations; and Class IV involves significant symptoms at rest, with severe to total physical activity limitations. Typically, an individual progresses through the classes as they live with the condition.

Although CHF is generally thought of as a chronic, progressive condition, it also can develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema and dyspnea.

Common treatment agents for CHF include vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have become standard agents for treating mild to moderate heart failure. Lowes et al, Clin. Cardiol., 23:III11-6 (2000).

Positive inotropic agents include beta-adrenergic agonists, such as dopamine, dobutamine, dopexamine, and isoproterenol. Use of a beta-agonist has potential complications, however, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., Fundam. Clin. Pharmacol., 15: 95-109 (2001). Accordingly, they have become an established therapy for heart failure. Even subjects that improve under beta-antagonist therapy may subsequently decompensate, however, and require acute treatment with a positive inotropic agent. Unfortunately, as their name suggests, beta-antagonists block the mechanism of action of the positive inotropic beta-agonists that are used in emergency care centers. Bristow et al., J. Card Fail., 7: 8-12 (2001).

In embodiments in which HNO in the gas phase is used to treat patients suffering from heart failure, another active agent that treats heart failure also can be administered. In one such embodiment, HNO in the gas phase can be administered in conjunction with a positive inotrope, such as a beta-agonist. Examples of beta-agonists include, without limitation, dopamine, dobutamine, isoproterenol, analogs of such compounds and derivatives of such compounds. In another embodiment, HNO in the gas phase can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Vasodilators, such as nitroglycerin, have been used for a long period of time to treat heart failure. The cause of nitroglycerin's therapeutic effect was not known until late in the last century, however, when it was discovered that the nitric oxide molecule (NO) was responsible for nitroglycerin's beneficial effects. In some subjects experiencing heart failure, a nitric oxide donor is administered in combination with a positive inotropic agent to both cause vasodilation and to increase myocardial contractility. This combined administration, however, can impair the effectiveness of positive inotropic treatment agents. For example, Hart et al, Am. J. Physiol. Heart Circ. Physiol., 281:146-54 (2001) reported that administration of the nitric oxide donor sodium nitroprusside, in combination with the positive inotropic, beta-adrenergic agonist dobutamine, impaired the positive inotropic effect of dobutamine. Hare et al., Circulation, 92:2198-203 (1995) also disclosed the inhibitory effect of nitric oxide on the effectiveness of dobutamine.

Further, as described in U.S. Pat. No. 6,936,639, compounds that donate nitroxyl (HNO) under physiological conditions have both positive inotropic and lusitropic effects and offer significant advantages over existing treatments for failing hearts. Due to their concomitant positive inotropic/lusotropic action and unloading effects, nitroxyl donors were reported as helpful in treating cardiovascular diseases characterized by high resistive load and poor contractile performance. In particular, nitroxyl-donating compounds were reported as useful in the treatment of heart failure, including heart failure in individuals receiving beta-antagonist therapy.

3. Ischemia Reperfusion Injury

In another embodiment, the presently disclosed subject matter provides a method for treating, preventing or delaying the onset and/or development of ischemia/reperfusion injury, the method comprising administering HNO in the gas phase as disclosed herein to a subject in need thereof.

In a particular embodiment, the method is for preventing ischemia/reperfusion injury. In a particular embodiment, HNO in the gas phase is administered prior to the onset of ischemia. In a particular embodiment, HNO in the gas phase is administered prior to procedures in which myocardial ischemia can occur, for example an angioplasty or surgery, such as a coronary artery bypass graft surgery. In a particular embodiment, HNO in the gas phase is administered after ischemia, but before reperfusion. In a particular embodiment, HNO in the gas phase is administered after ischemia and reperfusion.

In another embodiment, HNO in the gas phase can be administered to a patient who is at risk for an ischemic event. In a particular embodiment, HNO in the gas phase is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event.

Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction, elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, myocardial infarction (MI) and neurovascular ischemia, such as a cerebrovascular accident (CVA).

In another embodiment, the subject to be treated is an organ that is to be transplanted. In a particular embodiment, HNO in the gas phase can be administered prior to reperfusion of the organ in a transplant recipient. In a particular embodiment, HNO in the gas phase can be administered prior to removal of the organ from the donor, for example through the perfusion cannulas used in the organ removal process. If the organ donor is a live donor, for example a kidney donor, HNO in the gas phase can be administered to the organ donor. In a particular embodiment, HNO in the gas phase is administered while storing the organ. In a particular embodiment, HNO in the gas phase is administered such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, Postgrad. Med. 107(6):34-50 (2000).

Further, complications of untreated infectious diarrhea in the elderly can include myocardial, renal, cerebrovascular and intestinal ischemia. Slotwiner-Nie et al., Gastroenterol. Clin. N. Amer. 30(3):625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

4. Pulmonary Hypertension

As used herein, the term "pulmonary hypertension" or "PH" refers to a condition in which the pulmonary arterial pressure is elevated. The current hemodynamic definition of PH is a mean pulmonary arterial pressure (MPAP) at rest of greater than or equal to 25 mmHg Badesch et al., J. Amer. Coll. Cardiol. 54(Suppl.):S55-S66 (2009).

Accordingly, in another embodiment, HNO in the gas phase can be used to prevent or delay the onset and/or development of pulmonary hypertension. In one such embodiment, HNO in the gas phase can be used to prevent or delay the onset and/or development of pulmonary arterial hypertension (PAH).

In another embodiment, the disclosure provides a method of reducing mean pulmonary arterial pressure (MPAP), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

5. Cancerous Diseases

In some embodiments, the presently disclosed subject matter provides a method for treating, preventing or delaying the onset and/or development of a cancerous disease, comprising administering an effective amount of HNO in the gas phase as described herein to a subject in need thereof.

In some embodiments, the subject has or is suspected of having a cancerous disease, e.g., cancer.

Cancers that may be treated by the methods described herein include, without limitation, cancers of the head and neck, which include tumors of the head, neck, nasal cavity, paranasal sinuses, nasopharynx, oral cavity, oropharynx, larynx, hypopharynx, salivary glands, and paragangliomas; cancers of the liver and biliary tree, such as hepatocellular carcinoma; intestinal cancers, such as colorectal cancer; ovarian cancer; small cell and non-small cell lung cancer; breast cancer sarcomas, such as fibrosarcoma, malignant fibrous histiocytoma, embryonal rhabdomyosarcoma, leiomyosarcoma, neurofibrosarcoma, osteosarcoma, synovial sarcoma, liposarcoma, and alveolar soft part sarcoma; neoplasms of the central nervous systems, such as brain cancer; lymphomas, such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

In some embodiments, the method further comprises administering an effective amount of an additional therapeutic agent to the individual. In some embodiments, the additional therapeutic agent is an anti-cancer agent or a cytotoxic agent. Examples of such agents include, without limitation, alkylating agents, angiogenesis inhibitors, anti-metabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include, for example, beta-lapachone, ansamitocin P3, auristatin, bicalutamide, bleomycin, bleomycin, bortezomib, busulfan, calicheamycin, callistatin A, camptothecin, capecitabine, cisplatin, cryptophycins, daunorubicin, docetaxel, doxorubicin, duocarmycin, dynemycin A, etoposide, floxuridine, floxuridine, fludarabine, fluoruracil, gefitinib, gemcitabine, hydroxyurea, imatinib, interferons, interleukins, irnnotecan, methotrexate, mitomycin C, oxaliplatin, paclitaxel, spongistatins, suberoylanilide hydroxamic acid (SAHA), thiotepa, topotecan, trichostatin A, vinblastine, vincristine and vindesine.

In certain embodiments, the method includes reducing a need for assisted ventilation. In particular embodiments, the need for assisted ventilation is induced by pneumonia or one or more other acute respiratory syndromes.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

As used herein, the term "effective amount" refers to such amount of a therapeutic agent, which in combination with its parameters of efficacy and potential for toxicity, as well as based on the knowledge of the practicing specialist, should be effective in a given therapeutic form. As is understood in the art, an effective amount can be administered in one or more doses.

"Treatment," "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent," "preventing" and the like refers to reducing the probability of developing a condition in a subject who does not have, but is at risk of developing a condition. A subject "at risk" may or may not have a detectable condition, and may or may not have displayed a detectable condition prior to the treatment methods disclosed herein. "At risk" denotes that a subject has one or more so-called risk factors, which are measurable parameters that correlate with development of a condition and are known in the art. A subject having one or more of these risk factors has a higher probability of developing the condition than a subject without such risk factor(s).

"Unit dosage form" refers to a physically discrete unit suitable as a unitary dosage for a human or an animal. Each unit dosage form can contain a predetermined amount of a therapeutic agent calculated to produce a desired effect.

The term "combination" is used in its broadest sense and means that a subject is administered at least two agents, more particularly HNO in the gas phase and at least one additional therapeutic agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days.

The timing of administration of HNO in the gas phase and at least one additional therapeutic agent can be varied so long as the beneficial effects of the combination of these agents are achieved. Accordingly, the phrase "in combination with" refers to the administration of HNO in the gas phase and at least one additional therapeutic agent either simultaneously, sequentially, or a combination thereof. Therefore, a subject administered a combination of HNO in the gas phase and at least one additional therapeutic agent can receive HNO in the gas phase and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where HNO in the gas phase and at least one additional therapeutic agent are administered simultaneously, they can be administered to the subject as separate pharmaceutical compositions, each comprising either HNO in the gas phase or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of HNO in the gas phase and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A+Q_b/Q_B=\text{Synergy Index(SI)}$$

wherein:

- $Q_A$ is the concentration of a component A, acting alone, which produced an end point in relation to component A;
- $Q_a$ is the concentration of component A, in a mixture, which produced an end point;
- $Q_B$ is the concentration of a component B, acting alone, which produced an end point in relation to component B; and
- $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Solid-Gas Reactions for Nitroxyl (HNO) Generation in the Gas Phase

1.1 Overview

A new method for HNO generation in the gas phase is disclosed. In some embodiments, the method involves a reaction between a gaseous base and solid HNO donors corresponding to different families. Detection of HNO was carried out both indirectly, for example, by measuring the nitrous oxide ($N_2O$) byproduct of HNO dimerization using infrared spectroscopy, and directly, for example, by using mass spectrometry techniques and an electrochemical HNO sensor. The presently disclosed approach provides a new platform for studying HNO chemistry in the gas phase and its possible applications.

1.2 Background

Nitroxyl (azanone, HNO) is an inorganic small molecule that has been widely studied due to its high biological significance. Doctorovich et al., 2016; Fukuto, 2019. HNO is an expected intermediate in biochemical pathways, Doctorovich et al., 2014; Flores-Santana et al., 2011, and has reported medical applications regarding its cardioprotective action. Tocchetti et al., 2007; Guo et al., 2019; Sun et al., 2020.

This elusive, highly reactive species, as well as the related compound nitric oxide (NO), has been found to exert beneficial physiological effects, some of its own, and some overlapping those of NO. Suarez et al., 2020; Ma et al., 1999; Miranda et al., 2003. The medical use of HNO as an agent to prevent cardiac arrest, Fukuto, 2019, as a vasodilator, Velagic et al., 2020, and as an antibacterial agent, Galizia et al., 2018, is being developed by the use of HNO donors in solution.

Once formed, HNO readily reacts toward biological targets and itself, dimerizing to yield nitrous oxide ($N_2O$) and water (Scheme 1, Eqn. c). Shafirovich and Lymar, 2002. Therefore, a more controlled way to generate HNO efficiently can be achieved using HNO donors in situ.

The first HNO donor, reported in 1896, is Angeli's salt, $Na_2N_2O_3$, Angeli, 1896, which is still widely used in biological experiments. Since then, several HNO donor compounds have been developed. Basudhar et al., 2017. Amongst them, there is an important set of compounds, known as Piloty's acid derivatives (PA). Adas et al., 2018; Smulik-Izydorczyk et al., 2019; Sirsalmath et al., 2013; Porcheddu et al., 2009.

HNO generation from PA compounds takes place in two steps (Scheme 1a) involving the fast deprotonation of the sulfohydroxamic moiety followed by the slow release of HNO. The rate of HNO formation depends on each derivative's pKa, exhibiting a wide range in aqueous solution, between −1 and 9, influenced by the ring substitution pattern. Adas et al., 2018; Smulik-Izydorczyk et al., 2019; Sirsalmath et al., 2013; Porcheddu et al., 2009.

Piloty's acid and its derivatives have been used as HNO donors in different reactions. Carrone et al, 2017; Toscano et al., 2019. Most of these reactions are performed in aqueous solution, and only a few employ a non-liquid phase as a solvent. Harteck, 1933; Clyne and Thrush, 1961; Clyne and Thrush, 1962.

The main disadvantage of non-liquid phase experiments is the need for extreme conditions, such as high or low temperatures. The search for new HNO generation methods is then of great interest and the possibility of performing the reaction without involving liquid phases emerges as a new and promising strategy for the use of gaseous HNO in chemical or medical applications. Moreover, developing a system for the controlled generation of gaseous HNO may allow for the study of its reactivity in the gas phase beyond the well-known dimerization, such as its reaction towards molecular oxygen.

Some controversy, however, remains in this regard, since both peroxynitrite and $NO\text{-}+HO_2^-$ (hydroperoxide radical) have been proposed as possible products in solution. Fukuto et al., 1993; Smulik et al., 2014; Chazotte-Aubert et al., 1999. Due to further reactivity of any of the proposed products, the study of these systems is not an easy task; therefore, the generation of HNO in the gas phase by simple chemical methods might shed some light on this matter. Doctorovich et al., 2016; Suarez et al., 2020.

1.3 Scope

The presently disclosed subject matter, in some embodiments, examines the reaction of solid Piloty's acids derivatives with a gaseous base (e.g., $NH_3$ (g)). The results showed that this method is a facile and economical way to generate HNO that avoids the use of liquid phases or extreme experimental conditions. Similar studies with another base-catalyzed HNO donor, a (hydroxylamino)pyrazolone (HAPY) derivative, demonstrate the generality of this approach.

Accordingly, in some embodiments, the presently disclosed subject matter provides a novel nitroxyl (HNO) generation method, which avoids the need of using a liquid system or extreme experimental conditions. The presently disclosed method involves a reaction between a gaseous base and an HNO donor in the solid phase, thereby allowing the formation of gaseous HNO in a fast and economical way. Detection of HNO was carried out indirectly, measuring the nitrous oxide ($N_2O$) byproduct of HNO dimerization using infrared spectroscopy, and directly, using mass spectrometry techniques and an electrochemical HNO sensor.

1.4 Experimental

1.4.1 Materials and Methods

Commercially available reagents from Sigma Aldrich were used as received. Piloty's acid derivatives N-hydroxy-4-nitrobenzenesulfonamide ($NO_2$-PA) and N-hydroxy-4-fluorobenzenesulfonamide (F-PA) were synthesized from the corresponding benzene-sulfonyl chloride and hydroxylamine hydrochloride in the presence of MgO, according to literature methods. Porcheddu et al., 2009. The products were further purified using a silica gel chromatography column as reported independently. Porcheddu et al., 2009.

4-(N-Hydroxylamino)-4-(acetyl-O-methyoxyoxime)-N-phenyl-3-methylpyrazolone (HAPY-1) was synthesized according to literature procedure. Guthrie et al., 2015. The identity and purity of the resulting compounds were monitored by $^1$H NMR spectroscopy. Ammonia was generated by adding $NH_4OH$ solution to sodium hydroxide pellets in a sealed evacuated flask. Gas was allowed to evolve until the reaction became less vigorous. The amount of gaseous water present in the flask following this procedure was estimated to be <3% in moles under the experimental conditions (298K, 1 atm). Since gaseous water does not react with $NO_2$-PA, the observed results are exclusively due to reaction with $NH_3$(g).

1.4.1.1 NMR Spectroscopy $^1$H NMR spectroscopy measurements were carried out using a BRUKER Avance Neo 500 MHz spectrometer using d6-DMSO purchased from Sigma Aldrich as a solvent.

1.4.1.2 IR Measurements

IR measurements were made with a Thermo Nicolet Avatar 320 FT-IR spectrometer, using a five-centimeter long gas cell with NaCl windows. In a standard experiment, approximately 3.5 mg of PA derivative was placed inside the mounted cell, which was afterwards purged with a continuous argon flow and sealed with septa. For each experiment, approximately 15-20 mL of gaseous $NH_3$ in the flask were extracted with a syringe and injected into the IR cell. 8-scan measurements were continuously made until transmittance changes were no longer observed.

1.4.1.3 Electrochemical HNO Detection

HNO detection also was carried out with a previously described method based on a three-electrode system consisting of platinum counter electrode, Ag/AgCl reference electrode, and a gold working electrode modified with a cobalt porphyrin covalently attached via a 1-decanethiol moiety. Suhrez et al., 2013; International PCT Patent Application Publication No. WO2020/136414 A1, for HNO Biosensor, to Doctorovich et al, published Jul. 2, 2020, which is incorporated herein in its entirety. The method has been demonstrated to be specific for HNO, showing no interference or spurious signal due to the presence of NO, $O_2$, $NO_2^-$, and other RNOS. Suhrez et al., 2013; International PCT Patent Application Publication No. WO2020/136414 A1, for HNO Biosensor, to Doctorovich et al, published Jul. 2, 2020, which is incorporated herein in its entirety.

1.4.1.4 MS Measurements 1.4.1.4.1 Procedure #1

Gaseous products developed from solid $NO_2$—PA in the presence of 100 mbar of anhydrous ammonia were identified on-line using a capillary-based interface to a high-pressure (1-1000 mbar) Leybold Topatron-B radiofrequency mass spectrometer (MS). The setup (see Section 1.6.8) consists of a 0.5-$cm^3$ stainless steel reaction vessel that is continuously sampled with the mass analyzer. The vessel containing the $NO_2$-PA powder is connected to an ancillary gas handling system, through which gaseous $NH_3$ is put in contact with the solid. f A combination of a metering valve and a very narrow capillary is used to finely adjust the flow sampled by the MS. The temperature of the vessel and MS interface is adjusted to 90° C. during the experiments. The low internal volume of the interface region provides a response time of less than 15 seconds, while a complete mass spectrum is recorded in less than 10 seconds. The data are constantly acquired in a digital oscilloscope.

Gaseous products generated in the reaction of an aqueous solution containing 10-mM of $NO_2$-PA, at pH=10, were analyzed by the same MS procedure to validate the detection (and fragmentation) of the product $N_2O$.

1.4.1.4.2 Procedure #2

Products from the reaction of solid $NO_2$-PA and $NH_3$ (g) also were monitored using a Hiden EI mass spectrometer. Cline et al., 2011. $NO_2$-PA (10 mg) or HAPY-1 (10 mg) was placed into a 25 mL glass reaction vessel which was evacuated with a vacuum pump. The reaction vessel was connected to the mass spectrometer through a fused silica capillary (0.10-mm ID, 25 ft) and 10 mL of anhydrous $NH_3$ (g) from AirGas was injected into the reaction vessel using a 10-mL gas tight syringe to initiate the reaction. The rate of $NH_3$ addition was controlled by using a programmable syringe pump. Products were monitored for 25 minutes with continuous sampling.

1.5 Results and Discussion

When solid N-hydroxy-4-nitrobenzenesulfonamide ($NO_2$-PA) is exposed to gaseous ammonia, the solid's color turns from pale yellow to orange, and $N_2O$ evolution is observed by gas-phase IR spectroscopy. To study the reaction kinetics associated with HNO generation in heterogeneous phase, IR spectra were collected during the reaction between an excess of ammonia and solid $NO_2$-PA (in approximately 50:1 molar ratio). After injecting the gaseous base inside the IR cell, gas phase measurements were performed, monitoring the appearance of the characteristic $N_2O$ signal (2250-2150 $cm^{-1}$), Heinecke et al., 2013, the intensity of which was found to increase with time (FIG. 1). Full spectra for one of the experiments can be found in Section 1.6.1.

Kinetic results, shown in FIG. 1B, indicate two different processes over relatively short timescales: a short induction period, evidenced by a fast growth of the $N_2O$ signal following a first-order process, and, a few minutes later, a linear dependence of the signal as a function of time, denoting that zero-order kinetics dominates after induction. A possible explanation for this behavior might be that the $N_2O$ signal growth experimentally observed during the first seconds is dependent on the rate of $NH_3$ adsorption and on the efficiency of the gas phase mixing and diffusion process (Process 1, $k_0$). A second phase begins when an equilibrium $NH_3$ concentration is reached over the surface of the solid. Under these conditions, the concentration of $N_2O$ grows linearly as a function of time (order 0 regime, Process 2, $k_{R\times N}$), until reactive sites begin to become scarce. For more details, see Section 1.6.2. Other IR experiments and kinetic fittings are shown in Section 1.6.3.

Taking into account that $N_2O$ in the present reaction is only produced by HNO dimerization, Shafirovich and Lymar, 2002, the degree of $N_2O$ generation, $\alpha P$, was calculated as a function of time using the IR spectroscopy measurements at 2237 $cm^{-1}$ and compared to theoretical values, resulting in a first order kinetic regime (FIG. 1B, Section 1.6.2). The calculated rate constant (k) associated to the first process was equal to $k_0=(7\pm2)\times10^{-2}$ $s^{-1}$. The rate constant for the second (linear) process ($k_{R\times N}$) is ca. $10^{-8}$ $M\cdot s^{-1}$. There is a large error for the rate constant associated with this second process, because its rate likely depends on particle size, porosity, and other factors (see below).

Crushing the solid with a mortar and pestle did not produce a noticeable increase on the reaction rate and total $N_2O$ yield, presumably because this process only decreased aggregation (see Section 1.6.3), therefore not resulting in a net increase of available surface sites. Moreover, a small decrease was observed in the reaction rate, indicating that the solid particles were probably more compact after crushing. The complete set of calculated constants is shown in Table 1.

Since HNO's dimerization rate is faster than its production, as already described for aqueous solution, Shafirovich and Lymar, 2002; Bonner and Ko, 1992, it is possible to follow the production of HNO as a function of $\alpha P$ of the dimerization byproduct, $N_2O$. Scheme 1 shows the mechanism of HNO generation from PA in aqueous solution (a), a plausible reaction path for the heterogeneous (solid-gas) reaction studied in this work (b), and the dimerization and dehydration reaction of HNO (c) ($k_{DIM}=8\times10^6$ $M^{-1}s^{-1}$). Likewise, if the deprotonation rate of solid PA (Scheme 1, Eq. b2) is greater than the generation rate of HNO (Scheme 1, Eq. b3), the latter reaction will be, chemically speaking, the limiting step of the overall production of HNO, together with the surface kinetics described before. The first-order rate constant $k_0$ obtained for the formation of HNO from $NO_2$-PA (s)+$NH_3$ (g) during the first few minutes of reaction is similar to the one obtained for HNO generation from $NO_2$-PA (aq) in basic solution ($4.4\times10^{-2}$ $s^{-1}$, pH=10, T=298 K), Adas et al., 2018; Smulik-Izydorczyk et al., 2019; Sirsalmath et al., 2013; Porcheddu et al., 2009; Carrone et al, 2017; Toscano et al., 2019, and, as expected, faster than the rate constant obtained at pH 5. Adas et al., 2018; Smulik-Izydorczyk et al., 2019; Sirsalmath et al., 2013; Porcheddu et al., 2009; Carrone et al, 2017; Toscano et al., 2019. This observation suggests that in both cases the mechanism could be the same (PA deprotonation followed by decomposition), except that in the present case the diffusion of the gases and the presence of available sites on the solid surface affect the kinetics. Carrone et al, 2017; Bonner and Ko, 1992.

Scheme 1. (a) Mechanism of HNO generation in aqueous solution, (b) proposed heterogeneous (solid-gas) reaction path, and (c) nitroxyl dimerization and dehydration.

a) HNO generation in aqueous solution:

1.

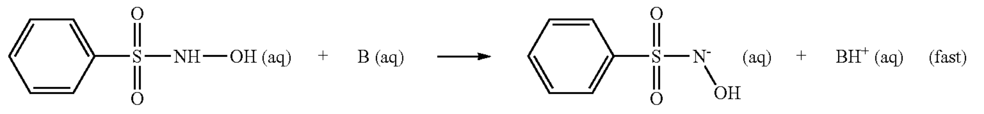

2.

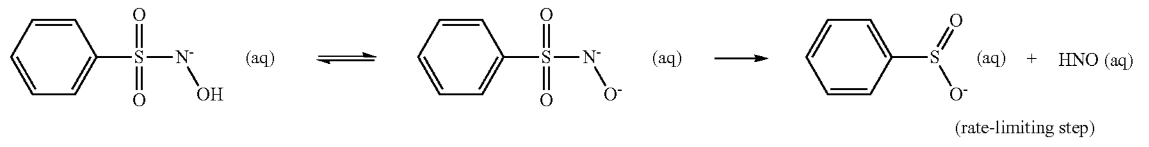

b) Heterogeneous HNO generation:

1.

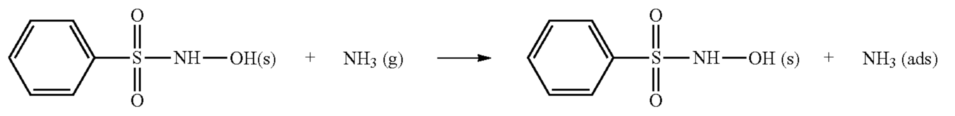

-continued

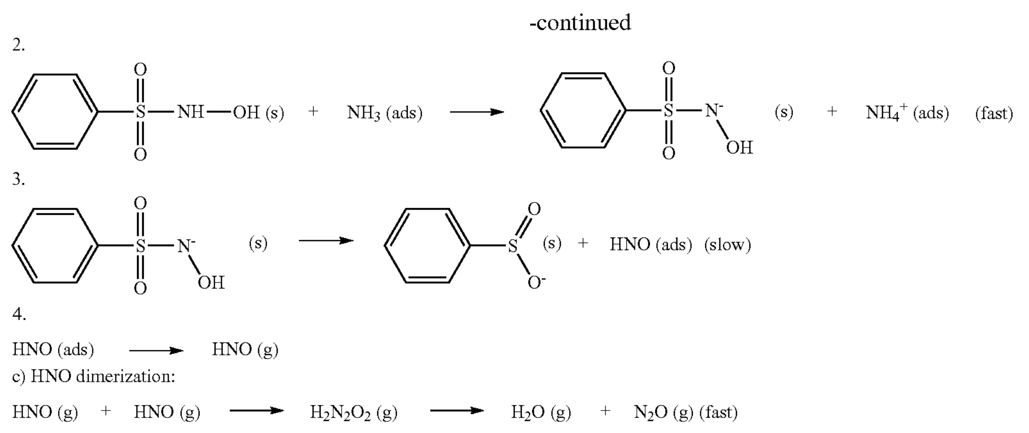

Evidence shows that small amounts of gaseous $H_2O$ or $O_2$ do not interfere, as the same behavior was observed in the absence and presence of $H_2O$ and $O_2$. Formation of $N_2O$ was also observed by using gaseous triethylamine instead of ammonia and displayed the same behavior. For more details, see Section 1.6. These results show that other basic compounds in the gaseous phase could be used for HNO generation, without the need of maintaining a completely anhydrous or anaerobic system, making this an easy method to obtain gaseous HNO in a fast way.

Reaction of $NH_3$ and another PA derivative, N-hydroxy-4-fluorobenzenesulfonamide (F-PA), was also followed by IR spectroscopy, showing the same behavior as observed for $NO_2$-PA. Results are shown in FIG. 16 and FIG. 17.

1.5.1 $N_2O$ Production Yield: Passivation

After building a calibration curve, the $N_2O$ production yield was calculated, which reached an approximate value of 25%±2% from FT-IR measurements (see Section 1.6.4). An independent $^1H$-NMR experiment showed that ca. 65% of the initial amount of $NO_2$-PA was still unreacted. The ca. 10% difference in the expected $N_2O$ yield (25% versus ca. 35% of $NO_2$-PA that has reacted) can be attributed to some $N_2O$ loss by unexpected leaks, and/or small amounts of adventitious $O_2$, which reacts with HNO (and the so produced NO will also react with HNO). Fukuto et al., 1993; Smulik et al., 2014; Chazotte-Aubert et al., 1999. The relatively small $N_2O$ yield suggests that gaseous ammonia readily reacts with the surface of the solid particle, with only little diffusion inside the particles, so that most solid remains unreactive.

1.5.2 Mass Spectrometry Measurements

Even though all results are consistent with the proposed mechanism (Scheme 1b), in order to eliminate any other possible mechanism for $N_2O$ formation, such as hyponitrite formation by direct reaction of two molecules of PA without effectively generating free HNO, the reaction was followed by mass spectrometry (MS) and using an electrochemical HNO sensor.

In the first case, the gaseous products developed in the reaction were identified on-line using a high-pressure (1-1000 mbar) radiofrequency mass spectrometer (Procedure #1). FIG. 2 shows a series of representative mass spectra taken during a typical experiment. The mass spectrum depicted in the upper panel was obtained by sampling 100 mbar of gaseous ammonia, before allowing contact with the $NO_2$-PA compound.

The main signal results from the $NH_3^+$ molecular ion (m/z 17), while smaller peaks at m/z 18 ($H_2O^+$) and 32 ($O_2^+$) reflect that some moisture and air were incorporated in the system during the injection. The spectrum in the next panel was taken approximately 15 seconds after the reaction started (t=0), maintaining the temperature at 90° C. Interestingly, clear evidence of the formation of $HNO^+$ is visible (molecular ion at m/z 31). A careful inspection of spectrum 2 in FIG. 2 allows one to recognize two very small signals accounting for $N_2O^+$ (m/z 44) and the fragmentation product $NO^+$ (m/z 30) as well, which can arise from $N_2O$ or HNO. Note that at this point the peaks of the contaminants $H_2O$ and $O_2$ present in the spectrometer have decreased due to pumping. The third spectrum, sampled from the reaction vessel one minute after the reaction started, reflects the situation in which the reaction leading to HNO is elapsed and, consequently, the $HNO^+$ signal at m/z 31 drops as a result of pumping, while those at m/z 30 ($NO^+$) and 44 ($N_2O^+$) are only barely visible.

The intense signals observed for $HNO^+$ in FIG. 2, especially in spectrum 2, indicates that under our experimental conditions HNO dimerization is relatively slow, in comparison with the same reaction in water, probably due to the absence of a solvent cage. Moreover, low pressure conditions in the reaction vessel and the manifold decreases the encounter probability of two HNO molecules.

Figure 3:
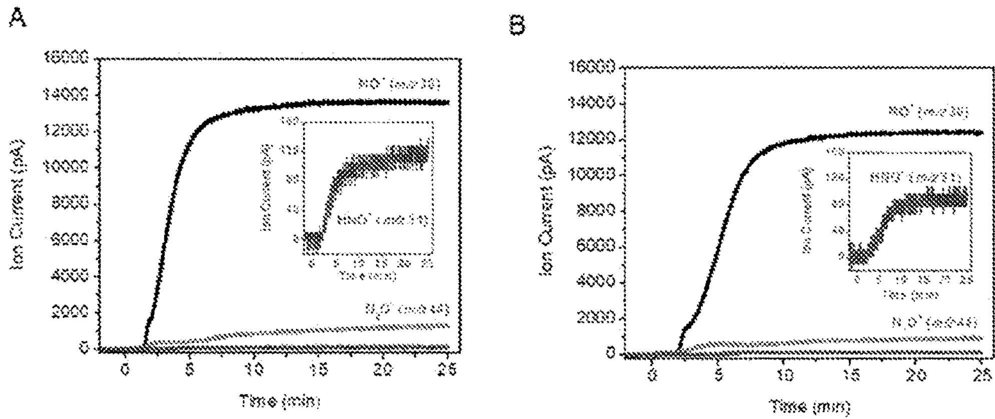

To validate the above new MS method used for HNO detection, the reaction was also followed by EI-MS using Procedure #2 (FIG. 3). With this method, masses m/z 30 ($NO^+$), 31 ($HNO^+$ or $^{15}NO^+$) and 44 ($N_2O^+$) were monitored in positive ion mode. Mixing of $NH_3$ (g) and $NO_2$-PA results in an increase in all three of these signals. The m/z 31 signal can arise from either HNO generation or from the naturally abundant $^{15}NO^+$ fragment of $N_2O$. From a series of $N_2O$ control experiments, the ratio of m/z 30 to m/z 31 from $^{15}NO^+$ is determined to be 255:1. A ratio smaller than 255:1 is, therefore, evidence for HNO generation. From the reaction of solid $NO_2$-PA with anhydrous $NH_3$ (g), the observed ratio of m/z 30 to 31 is 133:1. This corresponds to an m/z 31 signal that is approximately 50% $HNO^+$ while the other 50% is attributed to $^{15}NO^+$. Small amounts of $N_2O$ are also generated as a result of HNO dimerization.

We then examined if the rate of HNO release could be tuned by varying the rate at which $NH_3$ was introduced into the reaction flask. We varied the rate of $NH_3$ injection from 5 mL/min (FIG. 3A) to 2 mL/min (FIG. 3B) and found that this led to a slower observed release of HNO. The m/z 30 to 31 ratio was not changed by varying the rate of $NH_3$ addition. To examine if this reaction is possible with other base-catalyzed HNO donors, HAPY-1, a pyrazalone based HNO donor, was also incubated with $NH_3$ under the same conditions (Scheme 2, FIG. 19). HNO release was also confirmed from the reaction of HAPY-1 with $NH_3$ with an observed m/z 30 to 31 ratio of 172:1 (Section 1.6.8). This corresponds to an m/z 31 signal that is approximately 33% $HNO^+$ and 67% $^{15}NO^+$. While these donors have different half lives in solution, both donors released HNO at the same rate under these conditions based on the rate of $NH_3$ addition.

Scheme 2. Generation of HNO from HAPY-1.

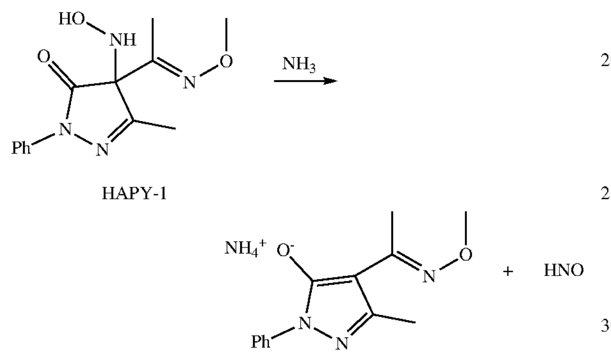

A much more intense HNO signal (m/z 31) is observed in the case of procedure #1. This is likely due to the higher temperature applied to the reaction, less HNO dilution, and a wider capillary used in the case of procedure #1. For more details, see Section 1.6.8.

Finally, to confirm the MS results indicating gaseous HNO generation, experiments using a selective electrochemical HNO sensor, Suárez et al., 2013; International PCT Patent Application Publication No. WO2020/136414 A1, for HNO Biosensor, to Doctorovich et al, published Jul. 2, 2020, which is incorporated herein in its entirety, were performed in aqueous solution (Section 1.6.9, FIG. 20 and FIG. 21).

1.6 Conclusions

Results show that gaseous HNO can be generated through a heterogeneous phase reaction, using a solid HNO donor and a gaseous base (such as $NH_3$), without the need of a liquid phase or extreme experimental conditions. Heating of the reaction mixture, combined with gas dilution and a fast flow, minimize the production of $N_2O$ by HNO dimerization, making it feasible to administer a gas containing HNO as the main species, as observed by MS (procedure #1).

A preliminary and compatible reaction scheme is shown in FIG. 4. When $NH_3$ (g) reaches the solid surface, the acid-base (I) reaction takes place. Then, PA decomposes (II) generating gaseous HNO. Finally, HNO dimerizes forming $N_2O$, and the remaining solid (III) is formed as PS—$NH_4^+$ (sulfinate).

As in aqueous solution, step (II), at short times, is limiting for HNO generation. When all PA on the surface of the solid is subsequently consumed, the diffusion process of the gaseous base through the solid and/or HNO diffusion from the solid to the gas phase limits the rate of HNO generation (as shown in FIG. 1B). The calculated rate constant of HNO generation during the first process ($k_0=7\times10^{-2}\ s^{-1}$) is similar to the one obtained in solution ($k=4.4\times10^{-2}\ s^{-1}$ at pH=10.7).[21] The HNO dimerization product ($N_2O$) was monitored by IR spectrometry, and HNO generation was confirmed by MS and a selective HNO sensor showing that this method could be a robust, fast, and economical technique for gaseous HNO generation.

This finding opens the gate for a study of new methods to achieve direct generation of this elusive molecule in the gaseous phase, dealing with non-liquid systems and friendlier experimental conditions than those previously reported. On one hand, HNO generation appears to be dependent on the rate of $NH_3$ administration rather than on the lifetime of donors in an aqueous solution, at least for the PA and HAPY donors (i.e., it could be possible to control the rate by the administration rate). On the other, preliminary experiments also were performed in a similar way to explore the reactivity of solid Angeli's salt, an acid-catalysed HNO donor, with gaseous HCl. $N_2O$ production was verified via FT-IR spectrophotometry and MS Procedure #1. Moreover, these new results can be used for the development of novel HNO sensors or other applications, such as medicinal and atmospheric use.

Lastly, another very interesting perspective that results from a simple and controlled generation of gaseous HNO (or even $N_2O$) is to provide a new drug delivery scheme that may be implemented in novel medical treatments. In particular, recent studies show that NO inhalation can reduce the need of assisted ventilation in conditions, such as pneumonia or other acute respiratory syndromes. Madjid and Casscells, 2004; Vetta et al., 2020; Kobayashi and Murata, 2020; Martel et al., 2020; Monsalve-Naharro et al., 2017.

In this context, considering the similarity in the vasodilating effects caused by NO and HNO, added to the antioxidant nature and specific pharmacology of HNO, make the medical administration of gaseous HNO worth studying. In this regard, although the presence of HCl or $NH_3$ can hinder them due to its toxicity, diverse methods could be engineered to eliminate the gaseous acid (or base) from the system. Some possibilities might include trapping the excess acid (or base) by using a membrane, or an aqueous basic (or acidic) solution. Wang and Chung, 2015; EL-Bourawi et al., 2007.

1.6 Supplemental Experimental Data

1.6.1 Infrared Spectra During the Reaction of $NO_2$-PA (s) and $NH_3$ (g)

FIG. 5 shows the IR spectra obtained during the reaction of $NO_2$-PA (s) and $NH_3$ (g) inside the IR gas cell.

1.6.2 Rate Constant Determination $Nh_3$ Adsorption:

$$v_1 = dn_{AD}/dt = k_1 * pNH_3 * (n_T - n_{AD}) = k_1' * (n_T - n_{AD})$$

Where $n_T$ accounts for the total amount of sites on the solid (which depends on particle size and porosity), and $n_{AD}$ represents the sites where $NH_3$ has adsorbed. $k_{1'} = k_1\ pNH_3$ since we can consider the pressure to be constant during the experiment.

$Nh_3$ Desorption:

$$v_{-1} = -dn_{AD}/dt = k_{-1} * n_{AD}$$

Gas-Solid Reaction on Solid Surface (Limiting Step):

$$v_{RXN} = k_{RXN} * n_{AD},$$

HNO Dimerization $$-d[\mathrm{HNO}]/dt = 2 * d[\mathrm{N_2O}]/dt,$$

as HNO generation is a first-order reaction with respect to $NH_3$ and PA concentration is constant (solid): Defining $\alpha_p$ as the degree of $N_2O$ formation and $\alpha_R$ as the degree of HNO formation, $d\alpha_p/dt=1-e^{-k't}$ and $d\alpha_R/dt=e-^{2k't}$ then, $k_{R\times N}=2*k_{N2O}'$.

The validity of the proposed mechanism can be analyzed taking into consideration the concentration time traces of the final reaction product, $N_2O$ (g). Three phases are expected to be observed, according to each timescale analyzed.

If $n_T$=total number of sites on the solid, and $n_{AD}$=number of sites occupied by adsorbed $NH_3$ molecules which have not reacted yet, then the difference between these two quantities represents the number of sites in which the reaction has already taken place: $n_R=n_T-n_{AD}$. (It is considered that the sites in which the reaction has taken place can no longer adsorb $NH_3$).

Initially, at short timescales, $n_R$ and $n_{AD}$ are negligible in comparison to $n_T$. $NH_3$ adsorption therefore prevails over its desorption, $n_{AD}/n_T$, which is the starting point for the heterogeneous phase reaction. The $N_2O$ IR signal growth experimentally observed during the first seconds is also dependent on the efficiency of the gas phase mixing process; particularly, $N_2O$ (g) diffusion from its generation site near the solid's surface to the optical path length of the IR gas cell.

A second phase begins when an equilibrium $NH_3$ concentration is reached over the surface of the solid. Under these conditions, $n_{AD}$ (eq)=$n_T$ $k_1*(k_1+k_{-1}\ pNH_3)^{-1}$, which remains roughly constant in the presence of ammonia excess while $n_{AD}+n_R<<n_T$ (intermediate timescales). Taking into consideration that during this second phase $V_{R\times N}=k_{R\times N}*n_{AD}$ (eq), it can be deduced that the concentration of $N_2O$ will grow linearly as a function of time (order 0 regime), until reactive sites begin to become scarce ($n_T\approx n_R$, and $n_{AD}\rightarrow 0$).

From there onwards, it is expected that the reaction rate drops to zero, and as a consequence, the concentration of $N_2O$ reaches a plateau. An interesting detail is that the final $N_2O$ concentration for all experiments is consistently about 30% of the expected amount for the complete reaction, which suggests that the reaction takes place only over the surface of the solid, leaving unreactive portions where the $NH_3$ gas cannot penetrate.

If the available sites on the surface of the solid are increased (e.g., by crushing), an increase in both the reaction rate and the saturation value should be expected. However, this was not observed experimentally, probably because the crushing process not only decreased particle size, but also compacted the material, therefore not resulting in a net increase of available surface sites (see FIG. 9 and FIG. 10).

If, on the other hand, $NH_3$ pressure is increased, an increase in the slope of the $N_2O$ concentration plot would be expected, and the saturation plateau would be reached faster since $n_{AD}$ (eq) would be larger. These last two issues will be further analyzed in a future work.

The complete set of calculated constants is shown in Table 1.

TABLE 1

Complete set of calculated constants for Process 1 and 2.

| | Calculated kinetic constants | | | |
|---|---|---|---|---|
| | Process 1 ($k_0$, $s^{-1}$) | | Process 2 ($k_{RXN}$, $M\ s^{-1}$) | |
| | Experimental results | | | |
| | Non-crushed solid | Crushed solid | Non-crushed solid | Crushed solid |
| | $3.6 \times 10^{-2}$, $4.0 \times 10^{-2}$, $5.0 \times 10^{-2}$, $6.0 \times 10^{-2}$, $6.0 \times 10^{-2}$[a], $7.0 \times 10^{-2}$[a], $7.0 \times 10^{-2}$[b], $7.0 \times 10^{-2}$, $7.0 \times 10^{-2}$, $8.0 \times 10^{-2}$[c], $8.0 \times 10^{-2}$, $8.0 \times 10^{-2}$, $1.1 \times 10^{-1}$ | $5.6 \times 10^{-2}$, $8.2 \times 10^{-2}$ | $2.8 \times 10^{-9}$, $8.4 \times 10^{-9}$, $1.1 \times 10^{-8}$, $1.6 \times 10^{-8}$, $5.4 \times 10^{-8}$, $4.2 \times 10^{-8}$, $5.0 \times 10^{-8}$, $8.8 \times 10^{-8}$, $1.0 \times 10^{-7}$, $1.5 \times 10^{-7}$ | $5.4 \times 10^{-9}$, $9.2 \times 10^{-9}$ |
| Average | $(7 \pm 2) \times 10^{-2}$ | $(7 \pm 2) \times 10^{-2}$ | $(5 \pm 4) \times 10^{-8}$ | $(7 \pm 3) \times 10^{-9}$ |
| Total average | $(7 \pm 2) \times 10^{-2}\ s^{-1}$ | | $(5 \pm 4) \times 10^{-8}\ M\ s^{-1}$ | |

[a] using dry ammonia. All other experiments were carried out using wet ammonia.
[b] using larger amounts of PA
[c] 15% of standard ammonia concentration.

The $N_2O$ molar concentration was calculated using the calibration curve shown below, using an experimental $\varepsilon\times 1$ constant of 436 $M^{-1}$, considering that the gas cell has a measured volume of 15 ml.

1.6.3 IR Absorbance Traces at 2237 $cm^{-1}$ During the Complete Reaction. Three-Phase Behavior Observed in Experiments with Crushed and Non-Crushed Solid FIG. 6, FIG. 7, and FIG. 8 show the absorbance traces at 2237 $cm^{-1}$ during complete reaction with $NH_3$ for crushed and non-crushed $NO_2$-PA solid. Hollow symbols represent estimative values (not measured). Fittings and fitting parameters are shown in the Figures and in Tables 2 and 3.

TABLE 2

Fitting parameters of plots shown in FIG. 7.

| Equation<br>y = A1*exp(−x/t1) + y0<br>Adj. R-Square | | | |
|---|---|---|---|
| 0.9893 | | 0.95402 | |
| | | Value | Standard Error |
| Non-crushed solid | y0 | 0.00887 | 1.54E−04 |
| Non-crushed solid | A1 | −0.00841 | 2.34E−04 |
| Non-crushed solid | t1 | 58.76006 | 4.33247 |
| Crushed solid | y0 | 0.00565 | 1.38E−04 |
| Crushed solid | A1 | −0.00515 | 3.08E−04 |
| Crushed solid | t1 | 39.26586 | 5.394 |

TABLE 3

Fitting parameters of plots shown in FIG. 8.

| Equation<br>y = a + b*x<br>Adj. R-Square | | | |
|---|---|---|---|
| 0.99655 | | 0.99473 | |
| | | Value | Standard Error |
| Non-crushed solid | Intercept | 0.00807 | 1.50E−04 |
| Non-crushed solid | Slope | 6.82E−06 | 8.55E−08 |
| Crushed solid | Intercept | 0.00586 | 2.36E−05 |
| Crushed solid | Slope | 1.13E−06 | 1.44E−08 |

A photograph of the non-crushed $NO_2$-PA particles, and selected measurements is shown in FIG. 9. A photograph of the $NO_2$-PA particles after crushing, and selected measurements is shown in FIG. 10.

1.6.4 $N_2O$ Production Yield Calculation

A calibration curve for $N_2O$ generation from $NO_2$-PA was built using FT-IR absorbance at 2236 $cm^{-1}$, which fitted the following equation with $R^2$=0.99913 Abs 2236 $cm^{-1}$ (AU)=0.0539. (μmol $N_2O$)$^{-1}$. μmol $N_2O$+0.0004 For the experiment of 3.5 mg crushed $NO_2$-PA solid reaction shown in main text, maximum absorbance reached at the plateau was 0.10 which corresponds to 2 μmol $N_2O$. Complete reaction of 3.5 mg (16 μmol $NO_2$-PA) should give 8 μmol $N_2O$, which results in a $N_2O$ production yield of 25%. This yield was verified by $^1$H NMR spectroscopy for a reaction using 10-mg $NO_2$-PA solid (FIG. 11 and FIG. 12).

The signals at 8.44 and 8.10 correspond to the reactant aromatic signals (2H each) (Aizawa, K. et al. *Bioorg. Med. Chem. Lett.* 2013, 23 (8), 2340-2343, Supplementary Information) while the signals at 8.18 and 7.70 (also 2H each) are assigned to the product. The relative sulfinate/total PA integrations (0.37, 37%) is similar to the observed $N_2O$ production yield calculated via IR analysis. The differences may be attributed to possible filtration in the gas cell, which might have caused some of the $N_2O$ to be lost, or some of the original HNO to be oxidized by reaction with molecular oxygen.

An internal 3 μL (57 μmol) $CH_3CN$ reference also was added to the NMR tube, which was used to verify that the total quantitative integration corresponding to the PA derivative and sulfinate add up to 97% of the initial 10 mg (see FIG. 12).

1.65 UV-Visible Spectra of Reactant and Products in Water

UV-Vis spectra of $NO_2$-PA in aqueous solution before (blue) and after (red) addition of $NH_4OH$, and solid obtained of PA (s)+$NH_3$ (g), dissolved in $D_2O$ (green) are shown in FIG. 13.

1.6.6. Determination of $N_2O$ Generation in Different Systems 10 mL of $NH_3$ (g) was introduced inside a 100-mL flask which contained 5 mg of $NO_2$-PA, and after 5 minutes a fraction of the gas contained in the flask was taken with a syringe and analyzed by IR spectrometry. For experiments with a dry and anaerobic atmosphere, the flask was purged with Ar. For the one that contained an aerobic atmosphere, the flask was not purged ($H_2O$ was considered null), and dry $NH_3$ (g) was used. In the case of the reaction in the presence of $O_2$ and $H_2O$, the flask was not purged and $NH_3$ (g) was taken from the headspace of an $NH_4OH$ (c) bottle. Results show no significant changes (FIG. 14).

The reaction was also carried out using gaseous triethylamine (TEA), instead of $NH_3$. Gas products were analyzed by IR spectroscopy, showing that $N_2O$ was formed. FIG. 15 shows the complete spectra obtained, and the region where the $N_2O$ characteristic signal appears is shown in the FIG. 15 inset.

1.6.7. Reaction of F-PA with Gaseous $NH_3$

The reaction also displayed a two-regime behavior, with an order 1 region (FIG. 16) followed by an order 0 region (FIG. 17).

1.6.8 MS Measurements

1.6.8.1 MS Measurements by Procedure #1

A schematic of the setup is shown in FIG. 18. It includes three main parts: reaction vessel, ancillary gas ($NH_3$) handling manifold, and interface to the mass analyzer. The reaction vessel (0.5 $cm^3$) is surrounded by an electrical heater that allows for temperature control with an uncertainty of ±1° C. It is connected to one (V1) of the four valve ports of a compact stainless-steel manifold, constructed using ⅛" tubing, the temperature of which can also be adjusted. The other three ports are respectively associated to: (V2), a vacuum line with a Pirani gauge, for adjusting and measuring the desired partial pressure of $NH_3$; (V3), a bottle with the reactive gas: in this case, anhydrous $NH_3$; and (V4), a direct (or via a low-volume trap-and-purge concentrator) access to the mass analyzer. The manifold-MS interface consists in a 60 cm long, 0.0025" ID, PEEK capillary connected to a low-pressure fine metering (18-turn) valve, which allows continuous and efficient sampling of the reaction gas phase (at pressures of hundreds of mbar) and its injection in the MS's electron-impact ion source. Flow rates up to 1 microliter per second of a 100-mbar gaseous reaction mixture can be sampled with our setup, maintaining the ion source pressure below $3\times10^{-6}$ mbar. The metering valve is used to fine adjust the flow sampled by the MS. The low internal volume of the interface region provides a response time of less than 15 seconds, while a complete mass spectrum is recorded in less than 10 seconds. The data is constantly acquired by a digital oscilloscope.

The procedure starts by introducing a small amount (ca. 2 mg) of N-hydroxy-4-nitro-benzenesulfonamide ($NO_2$-PA) in the reaction vessel and evacuating the system for a few minutes (V1 and V2 valves opened), maintaining the temperature at 90° C. At this temperature, no decomposition of the solid compound was observed in the MS in an independent experiment (V2 and V4 valves opened), even using a trap at liquid nitrogen temperature for 5 minutes, and analyzing its content with the MS once the trap was warmed to room temperature. The next step is to put the solid in contact with gaseous ammonia. First, the solid is isolated for a moment (V2 closed) and then 100 mbar of $NH_3$ is introduced into the manifold (V3 opened). The reaction vessel is filled with this gas (V2 opened) and the reaction begins. The gaseous mixture contained in the reaction vessel can finally be sampled in the MS (V2, V4 and V5 opened, V3 closed) during some minutes, recording one mass spectrum every 10 seconds.

Gaseous products generated in the reaction of an aqueous solution, at pH=10, containing 10 mM of $NO_2$-PA were analyzed using the same procedure, introducing the solution in the reaction vessel. In this case, a large water signal dominates the mass spectrum.

1.6.8.2 MS Measurements by Procedure #2

All analyses were done using a Hiden HAL3F-RC Quadrupole Mass Spectrometer (Hiden Analytical, Warrington, England, UK) with an SEM detector and ionization energy of 70 eV. A 25 foot fused silica capillary was connected to a 25 mL reaction vessel containing the solid HNO donor. Ion source pressure was maintained below $2.0\times10^{-5}$ Torr throughout the course of the experiment. The reaction was monitored with continuous sampling for 25 minutes following the addition of anhydrous $NH_3$ (g).

Mass spectrum recorded from the reaction of HAPY-1 and anhydrous $NH_3$ (g) at RT by Procedure #2 are shown in FIG. 19. The mass spectrum in FIG. 19A was recorded with an $NH_3$ addition rate of 5 mL/min, and the mass spectrum in FIG. 19B was recorded with an $NH_3$ addition rate of 2 mL/min.

The observed differences in the mass spectrometry procedures #1 and #2 respond to changes in the experimental conditions. The difference in operation temperatures is important: 90° C. in procedure #1 versus 25° C. in #2. HNO gets released faster at higher temperatures and has less time to react (hence the shorter ejection time in procedure #1). Also, the capillary used to restrict the pressure between the reactor and the MS vacuum chamber (in both cases ca. 10-6 mbar) is wider in procedure #1. These factors make the HNO get to the MS much faster in procedure #1 (ca. 15 s versus 4 minutes in the case of procedure #2). Therefore, the HNO signal m/z=31 is more intense in the case of procedure #1.

1.6.9 HNO Determination

HNO generation was also assessed using an electrochemical HNO sensor. For these experiments, the experimental set up shown in FIG. 20, in which 5 mg $NO_2$PA were placed over a filter paper and cotton filter inside the plastic end of a disposable needle, which was used with a glass 10 ml syringe.

Initially, the syringe was connected to an "empty needle", and was thoroughly purged with Ar. The gas of interest (argon for the blank experiments and a gaseous $NH_3$—Ar solution for the reaction) was collected using the empty needle, which was only changed for the PA-charged needle immediately before the experiments. The gas was allowed to flow into a $KNO_3$ solution in which the HNO-sensitive electrode was placed, and the current signal was registered. (FIG. 21) A positive control using an ethanolic 1 mM $NO_2$PA solution was also performed. FIG. 21 shows the corresponding [HNO] vs time plot after the stepwise addition of ammonia:argon (1:10) mixture to 5 mg $NO_2$-PA.

1.6.10. DSC of $NO_2$-PA

A DSC plot for $NO_2$-PA is shown in FIG. 22.

Example 2

HNO Release by Thermal Decomposition of Piloty's Acid Derivatives

Referring now to FIG. 23, FIG. 24, and FIG. 25, experiments were performed with the Piloty's acid derivatives, N-hydroxy-4-nitrobenzenesulfonamide ($NO_2$-PA) and N-hydroxy-4-fluorobenzenesulfonamide (F-PA). Approximately 5 mg of solid PA derivative was placed under Ar for 30 minutes at different fixed temperatures of 60, 70, 80, 90 and 100° C., and the gas headspace was collected to determine if $N_2O$ (the product of HNO dimerization) was generated.

In FIG. 23, $N_2O$ absorbance/mole PA derivative was plotted as a function of temperature. F-PA appears to start decomposing above 80° C., and $NO_2$-PA above 90° C. As a reference, a green line indicates the $N_2O$/mole PA value corresponding to the maximum yield observed following treatment of $NO_2$-PA with $NH_3$ at room temperature, as described previously.

The approximate $N_2O$ yield for F-PA is 35% at 90° C. and 47% at 100%. For $NO_2$-PA, the $N_2O$ yield is approximately 54% at 100° C.

Differential scanning calorimetry (DSC) plots for both derivatives at 10° C./min are provided below in FIG. 23, FIG. 24, and FIG. 25:

$NO_2$-PA:

Starts decomposing at 131° C. and has a strong peak at 164° C. However, if heated for half an hour, as shown above, decomposition begins before 100° C.

F-PA:

Starts decomposing at 92° C. and has a strong peak at 117° C. However, if heated for half an hour, as shown above, decomposition begins before 90° C.

Example 3

Reaction of Angeli's Salt with Gaseous HCl

Additionally, experiments were performed in a similar way to explore the reactivity of solid Angeli's salt (AS), an acid-catalyzed HNO donor, with gaseous HCl. See scheme below for the generation of HNO from AS.

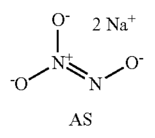
AS $H^+$

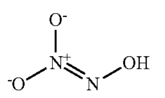

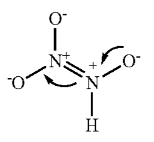

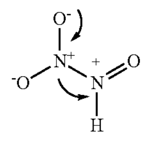

HNO + $NO_2^-$ $N_2O$ (the product of HNO dimerization) generation was verified via FT-IR spectroscopy and MS Procedure #1. The amount of produced $N_2O$ was followed as a function of time, and the rate corresponding to HNO formation was found to be $k=3\pm0.5\ 10^{-3}\ s^{-1}$.

3.1 Reaction of AS (s) and HCl (g) Followed by IR Spectroscopy

IR spectra were acquired after introducing approximately 20 mL of the headspace from a HCl bottle into a previously evacuated IR gas cell containing approximately 2 mg of AS (FIG. 26). The characteristic $N_2O$ signal is observed at 2200-2250 $cm^{-1}$. HCl and $H_2O$ signals are observed from 2500 $cm^{-1}$ and beyond. $CO_2$ is also observed (2300-2400 $cm^{-1}$).

FIG. 26 shows IR spectra obtained during the reaction of AS (s) with HCl (g).

FIG. 27 shows IR spectra region from 2300 to 2050 $cm^{-1}$ (right) and from 1900 to 1750 $cm^{-1}$, obtained during reaction of AS (s) with HCl (g). The signals at 2200-2250 $cm^{-1}$ are characteristic of $N_2O$, while the 2100-2150 $cm^{-1}$ and 1800 $cm^{-1}$ signals are assigned to CO and NO, respectively. The signals at ca. 1700 $cm^{-1}$ and 2275 $cm^{-1}$ remain unassigned.

The IR cell is not hermetically sealed, so there is likely some gas loss. Using the signal decay when reaction was assumed to be completed, a gas loss compensation correction was performed (FIG. 28). The calculated rate constant for $N_2O$ formation remained almost the same (FIG. 29).

FIG. 28 is the calculated absorbance at 2237 $cm^{-1}$ (black) and corrected absorbance considering the gas loss (white). Approximate $N_2O$ production yield: 2-4%.

FIG. 29 Left: Degree of product formation calculated using corrected absorbance at 2237 $cm^{-1}$ (dotted) and theoretical curve (1−eˆ(−kt), $k=1.5\times10^{-3}\ s^{-1}$); Right: Degree of product formation calculated using absorbance at 2237 $cm^{-1}$ (dotted) and theoretical curve (1-eˆ(−kt), $k=2.0\times10^{-3}\ s^{-1}$)

FIG. 30 shows $N_2O$ absorbance as a function of time calculated using % T at 2237 $cm^{-1}$ from two additional experiments. In both cases the reaction was not complete. Theoretical curves (1−eˆ(−kt), $k=1.5\times10^{-3}\ s^{-1}$) were fitted (FIG. 31) to obtain the value of the rate constant of $N_2O$ formation in both reactions shown in FIG. 30.

FIG. 30 is the calculated absorbance at 2237 $cm^{-1}$ (black) for two independent reactions.

FIG. 31 shows the degree of product formation (calculated using absorbance at 2237 $cm^{-1}$ (dotted) and theoretical curve (1−eˆ(−kt), $k=1.5\times10x^{-3}\ s^{-1}$) for both reactions (left and right) of FIG. 30.

Assuming that HNO dimerization is fast relative to its generation, the calculated rate of HNO generation is $3\times10^{-3}\ s^{-1}$.

Signals between 1900 and 1800 $cm^{-1}$ were analyzed using the data obtained in an additional experiment, where bands at 1870 $cm^{-1}$ could be observed better (FIG. 32). Absorbance values at 1809 and 1872 $cm^{-1}$ were calculated. A theoretical exponential curve was fitted with the data of corrected absorbance (at 1872 $cm^{-1}$) in order to obtain the rate constant of the product formation (FIG. 35). The k value found was equal to $6\times10^{-3}\ s^{-1}$.

FIG. 32 shows the IR spectral region from 2000 to 1700 $cm^{-1}$. Inset: Region where NO signal appears.

FIG. 33 is the calculated absorbance at 1809 $cm^{-1}$ (black) and 1872 $cm^{-1}$ (white).

FIG. 34 is the calculated (black) and corrected absorbance (white) at 1872 $cm^{-1}$.

FIG. 35 shows the degree of product formation (calculated using corrected absorbance at 1872 $cm^{-1}$ (dotted) and theoretical curve (1−eˆ(−kt), $k=6.0\times10^{-3}\ s^{-1}$)

3.2 Reaction ofAS (s) and HCl (g) Followed by MS

FIG. 36 shows the MS results obtained after the reaction of AS with HCl.

FIG. 36 shows the HCl MS spectra (top; exp 40) where isotopic signals are present (35-37 and 36-38) and MS spectra obtained during the reaction between gaseous HCl and AS (bottom; exp 45). NO is observed at m/z 30 and $N_2O$ at 44.

Example 4

Reaction Between Solid Cysteine and Gaseous Nitric Oxide

4.1 Experimental Procedure 100 mg of solid cysteine was placed in 7 mL vials. The solid cysteine was degassed through vacuum-purge cycles with high purity argon gas. Nitric oxide (NO) was generated anaerobically by dropwise addition of degassed water to a mixture of 4 g of $NaNO_2$, 8.5 g of $FeSO_4$, and 8.5 g of NaBr. The NO generated in this way was used without any further treatment.

To carry out the reaction, 2 mL of gaseous NO, equivalent to roughly 89 μmol, was introduced into the vials with 100 mg (825.35 μmol) of cysteine to obtain a reductant:NO ratio of approximately 10:1. As used herein, the terms "reductant" and "reducing agent" are used interchangeably. Next, 50 μL of degassed Milli-Q grade $H_2O$, or NaOH (0.1 M), or $H_3PO_4$ (0.1 M), or phosphate buffer (10 mM pH 7.2) was added to these vials, barely moistening the solid. The vials were capped with septa within an argon-filled Schlenk tube and subjected to magnetic stirring during the specified reaction time. After that time, the headspace of the vials was extracted and analyzed by FTIR spectroscopy, monitoring the vibrational frequency characteristic of nitrous oxide ($N_2O$) at 2212 and 2236 $cm^{-1}$. $N_2O$ is a product of nitroxyl (HNO) dimerization. These signals were compared to a calibration curve prepared by injecting samples of $N_2O$ produced in situ by decomposition of Angeli's salt (AS), a known HNO producer. All experiments were done in duplicates.

4.2 Results 4.2.1 FTIR

Referring now to FIG. 37, is a graph of $N_2O$ production versus time reaction under $H_2O$ humid conditions. As provided in FIG. 37, an increase in $N_2O$ production is observed as time progresses, at least up to six hours. In addition, measurements were made at 20 hours of reaction. $N_2O$ production, however, is notably lower and less reproducible between duplicates, giving indications that the system is beginning to lose $N_2O$.

For comparison purposes, measurements were made at 1 hour of reaction under the presence of $H_2O$ or 0.1 M NaOH or 0.1 M $H_3PO_4$, or 10-mM phosphate buffer pH 7.2 (FIG. 38). These results show $N_2O$ production in all the conditions analysed. The production is notably lower, however, when the reaction is carried out in the presence of $H_3PO_4$.

In addition, KBr pellets were prepared from the solids remaining from the reaction for analysis by FTIR. From these spectra, it was confirmed that cysteine is oxidized to the corresponding disulfide, cystine, after reacting with NO (FIG. 39). Similar results were obtained when analyzing the NMR spectra of these same solids.

4.2.2 MS

Subsequently, similarly to the experiment described above, the solid-gas reaction was carried out in the presence of moisture, in closed vials. Then, through an anaerobic connection system, the headspace of the reaction was delivered to a mass spectrometer where the m/z=44 signal corresponding to $N_2O$ was detected.

4.2.3 Reaction Between Other Solid Compounds and NO

Similar experiments were carried out for the reaction between Naringenin (a natural flavonoid present in citrus fruits), $Ni^{+2}$-Naringin, and dithionite $(S_2O_4)^{2-}$, and NO. These results confirmed the formation of $N_2O$ as the final product in each of these cases.

Generally, compounds with the following functional groups, or their corresponding metal complexes, are possible NO/HNO reducers in the solid-gas phase: alcohols and thiols, e.g., naringenin, $Ni^{+2}$-naringin, and cysteine, as well as reducing inorganic solids, e.g., dithionite.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Doctorovich, F.; Farmer, P. J.; Marti, M. A. *The Chemistry and Biology of Nitroxyl* (*HNO*); Elsevier, 2016; Vol. 53.

Fukuto, J. M. A Recent History of Nitroxyl Chemistry, Pharmacology and Therapeutic Potential. *Br. J. Pharmacol.* 2019, 176 (2), 135-146.

Doctorovich, F.; Bikiel, D. E.; Pellegrino, J.; Suárez, S. A.; Marti, M. A. Reactions of HNO with Metal Porphyrins: Underscoring the Biological Relevance of HNO. *Acc. Chem. Res.* 2014, 47 (10), 2907-2916.

Flores-Santana, W.; Salmon, D. J.; Donzelli, S.; Switzer, C. H.; Basudhar, D.; Ridnour, L.; Cheng, R.; Glynn, S. A.; Paolocci, N.; Fukuto, J. M.; Miranda, K. M.; Wink, D. A. The Specificity of Nitroxyl Chemistry Is Unique Among Nitrogen Oxides in Biological Systems. *Antioxid. Redox Signal.* 2011, 14 (9), 1659-1674.

Tocchetti, C. G.; Wang, W.; Froehlich, J. P.; Huke, S.; Aon, M. A.; Wilson, G. M.; Di Benedetto, G.; O'Rourke, B.; Gao, W. D.; Wink, D. A.; Toscano, J. P.; Zaccolo, M.; Bers, D. M.; Valdivia, H. H.; Cheng, H.; Kass, D. A.; Paolocci, N. Nitroxyl Improves Cellular Heart Function by Directly Enhancing Cardiac Sarcoplasmic Reticulum Ca 2+Cycling. *Circ. Res.* 2007, 100 (1), 96-104.

Guo, Y.; Xu, J.; Wu, L.; Deng, Y.; Wang, J.; An, J. Advances in Research on Treatment of Heart Failure with Nitrosyl Hydrogen. *Heart Fail. Rev.* 2019, 24 (6), 941-948.

Sun, H.-J.; Wu, Z.-Y.; Cao, L.; Zhu, M.-Y.; Nie, X.-W.; Huang, D.-J.; Sun, M.-T.; Bian, J.-S. Role of Nitroxyl (HNO) in Cardiovascular System: From Biochemistry to Pharmacology. *Pharmacol. Res.* 2020, 159, 104961.

Suarez, S. A.; Vargas, P.; Doctorovich, F. Updating NO·/HNO Interconversion under Physiological Conditions: A Biological Implication Overview. *J. Inorg. Biochem.* 2020.

Ma, X. L.; Gao, F.; Liu, G.-L. L.; Lopez, B. L.; Christopher, T. A.; Fukuto, J. M.; Wink, D. A.; Feelisch, M. Opposite Effects of Nitric Oxide and Nitroxyl on Postischemic Myocardial Injury. *Proc. Natl. Acad. Sci.* 1999, 96 (25), 14617-14622.

Miranda, K. M.; Paolocci, N.; Katori, T.; Thomas, D. D.; Ford, E.; Bartberger, M. D.; Espey, M. G.; Kass, D. A.; Feelisch, M.; Fukuto, J. M.; Wink, D. A. A Biochemical Rationale for the Discrete Behavior of Nitroxyl and Nitric Oxide in the Cardiovascular System. *Proc. Natl. Acad. Sci.* 2003, 100 (16), 9196-9201.

Velagic, A.; Qin, C.; Woodman, O. L.; Horowitz, J. D.; Ritchie, R. H.; Kemp-Harper, B. K. Nitroxyl: A Novel Strategy to Circumvent Diabetes Associated Impairments in Nitric Oxide Signaling. *Front. Pharmacol.* 2020.

Galizia, J.; Acosta, M. P.; Urdániz, E.; Marti, M. A.; Piuri, M. Evaluation ofNitroxyl Donors' Effect on Mycobacteria. *Tuberculosis* 2018, 109, 35-40. https://doi.org/10.1016/j.tube.2018.01.006.

Shafirovich, V.; Lymar, S. V. Nitroxyl and Its Anion in Aqueous Solutions: Spin States, Protic Equilibria, and Reactivities toward Oxygen and Nitric Oxide. *Proc. Natl. Acad. Sci. U.S.A* 2002, 99 (11), 7340-7345.

Angeli, A. Sopra La Nitroidrossilammina. *Gazz. Chim. Ital.* 1896, 26, 17-25.

Basudhar, D.; Bharadwaj, G.; Salmon, D. J.; Miranda, K. M. HNO Donors. In *The Chemistry and Biology of Nitroxyl* (*HNO*); *Elsevier,* 2017; pp 11-36.

Adas, S. K.; Bharadwaj, V.; Zhou, Y.; Zhang, J.; Seed, A. J.; Brasch, N. E.; Sampson, P. Synthesis and HNO Donating Properties of the Piloty's Acid Analogue Trifluoromethanesulphonylhydroxamic Acid: Evidence for Quantitative Release of HNO at Neutral PH Conditions. *Chem.—A Eur. J.* 2018, 24 (29), 7330-7334.

Smulik-Izydorczyk, R.; Rostkowski, M.; Gerbich, A.; Jarmoc, D.; Adamus, J.; Leszczynska, A.; Michalski, R.;

Marcinek, A.; Kramkowski, K.; Sikora, A. Decomposition of Piloty's Acid Derivatives—Toward the Understanding of Factors Controlling HNO Release. *Arch. Biochem. Biophys.* 2019, 661, 132-144.

Sirsalmath, K.; Suárez, S. A.; Bikiel, D. E.; Doctorovich, F. The PH of HNO Donation Is Modulated by Ring Substituents in Piloty's Acid Derivatives: Azanone Donors at Biological PH. *J. Inorg. Biochem.* 2013, 118, 134-139.

Porcheddu, A.; De Luca, L.; Giacomelli, G. A Straightforward Route to Piloty's Acid Derivatives: A Class of Potential Nitroxyl-Generating Prodrugs. *Synlett* 2009, 2009 (13), 2149-2153.

Carrone, G.; Pellegrino, J.; Doctorovich, F. Rapid Generation of HNO Induced by Visible Light. *Chem. Commun.* 2017, 53 (38), 5314-5317.

Toscano, J. P.; Brookfield, F. A.; GB; Cohen, A. D.; Courtney, S. M.; Frost, L. M.; Kalish, V. J. U.S. patent Ser. No. 10/487,049—N-Hydroxylsulfonamide Derivatives as New Physiologically Useful Nitroxyl Donors. 10487049, 2019.

Harteck, P. Die Darstellung von HNO Bzw. [HNO] N. *Berichte der Dtsch. Chem. Gesellschaft* (*A B Ser.* 1933, 66 (3), 423-426.

Clyne, M. A. A.; Thrush, B. A. Reaction of Nitrogen Dioxide with Active Nitrogen. *Trans. Faraday Soc.* 1961, 57, 69.

Clyne, M. A. A.; Thrush, B. A. Mechanism of Chemiluminescent Reactions Involving Nitric Oxide—the H+NO Reaction. *Discuss. Faraday Soc.* 1962, 33, 139-148.

Fukuto, J. M.; Hobbs, A. J.; Ignarro, L. J. Conversion of Nitroxyl (HNO) to Nitric Oxide (NO) in Biological Systems: The Role of Physiological Oxidants and Relevance to the Biological Activity of HNO. Biochem. *Biophys. Res. Commun.* 1993, 196 (2), 707-713.

Smulik, R.; Debski, D.; Zielonka, J.; Michalowski, B.; Adamus, J.; Marcinek, A.; Kalyanaraman, B.; Sikora, A. Nitroxyl (HNO) Reacts with Molecular Oxygen and Forms Peroxynitrite at Physiological PH. *J. Biol. Chem.* 2014, 289 (51), 35570-35581.

Chazotte-Aubert, L.; Oikawa, S.; Gilibert, I.; Bianchini, F.; Kawanishi, S.; Ohshima, H. Cytotoxicity and Site-Specific DNA Damage Induced by Nitroxyl Anion (NO—) in the Presence of Hydrogen Peroxide. *J Biol. Chem.* 1999, 274 (30), 20909-20915.

Aizawa, K.; Nakagawa, H.; Matsuo, K.; Kawai, K.; Ieda, N.; Suzuki, T.; Miyata, N. Piloty's Acid Derivative with Improved Nitroxyl-Releasing Characteristics. *Bioorg. Med. Chem. Lett.* 2013, 23 (8), 2340-2343.

Guthrie, D. A.; Ho, A.; Takahashi, C. G.; Collins, A.; Morris, M.; Toscano, J. P. "Catch-and-Release" of HNO with Pyrazolones. *J. Org. Chem.* 2015, 80 (3), 1338-1348.

Suárez, S. A.; Bikiel, D. E.; Wetzler, D. E.; Marti, M. A.; Doctorovich, F. Time-Resolved Electrochemical Quantification of Azanone (HNO) at Low Nanomolar Level. *Anal. Chem.* 2013, 85 (21), 10262-10269.

Doctorovich, F.; Suárez, S. A.; Marti, M. A.; Battaglini, F. International Patent "HNO Biosensor", WO2020/136414 A1, 2018.

Cline, M. R.; Tu, C.; Silverman, D. N.; Toscano, J. P. Detection of Nitroxyl (HNO) by Membrane Inlet Mass Spectrometry. *Free Radic. Biol. Med.* 2011, 50 (10), 1274-1279.

Heinecke, J. L.; Khin, C.; Pereira, J. C. M.; Suárez, S. A.; Iretskii, A. V; Doctorovich, F.; Ford, P. C. Nitrite Reduction Mediated by Heme Models. Routes to NO and HNO? *J. Am. Chem. Soc.* 2013, 135 (10), 4007-4017.

Bonner, F. T.; Ko, Y. Kinetic, Isotopic, and Nitrogen-15 NMR Study of N-Hydroxybenzenesulfonamide Decomposition: An Nitrosyl Hydride (HNO) Source Reaction. *Inorg. Chem.* 1992, 31 (12), 2514-2519.

Madjid, M.; Casscells, S. W. Of Birds and Men: Cardiologists' Role in Influenza Pandemics. *Lancet* 2004, 364 (9442), 1309.

Vetta, F.; Vetta, G.; Marinaccio, L. Coronavirus Disease 2019 (COVID-19) and Cardiovascular Disease: A Vicious Circle. *J Cardiol. Cardiovasc. Res.* 2020, 1 (2), 1-12.

Kobayashi, J.; Murata, I. Nitric Oxide Inhalation as an Interventional Rescue Therapy for COVID-19-Induced Acute Respiratory Distress Syndrome. Ann. Intensive Care 2020, 10 (1), 61.

Martel, J.; Ko, Y.-F.; Young, J. D.; Ojcius, D. M. Could Nasal Nitric Oxide Help to Mitigate the Severity of COVID-19*? Microbes Infect.* 2020.

Monsalve-Naharro, J. Á.; Domingo-Chiva, E.; Castillo, S. G.; Cuesta-Montero, P.; Jiménez-Vizuete, J. M. Inhaled Nitric Oxide in Adult Patients with Acute Respiratory Distress Syndrome. *Farmacia Hospitalaria.* 2017, 292-312.

Wang, P.; Chung, T.-S. Recent Advances in Membrane Distillation Processes: Membrane Development, Configuration Design and Application Exploring. *J. Memb. Sci.* 2015, 474, 39-56.

EL-Bourawi, M. S.; Khayet, M.; Ma, R.; Ding, Z.; Li, Z.; Zhang, X. Application of Vacuum Membrane Distillation for Ammonia Removal. *J. Memb. Sci.* 2007, 301 (1-2), 200-209.

S. Moncada, R. M. Palmer, E. A. Higgs, Nitric oxide: physiology, pathophysiology, and pharmacology., Pharmacol. Rev. 43 (1991) 109-42.

N. Paolocci, M. I. Jackson, B. E. Lopez, K. Miranda, C. G. Tocchetti, D. A. Wink, A. J. Hobbs, J. M. Fukuto, The pharmacology of nitroxyl (HNO) and its therapeutic potential: not just the Janus face of NO., Pharmacol. Ther. 113 (2007) 442-58.

H.-J. Sun, W.-T. Lee, B. Leng, Z.-Y. Wu, Y. Yang, J.-S. Bian, Nitroxyl as a Potential Theranostic in the Cancer Arena, Antioxid. Redox Signal. 32 (2020) 331-349.

M. E. Shoman, O. M. Aly, Nitroxyl (HNO): A Possible Strategy for Fighting Cancer, Curr. Top. Med. Chem. 16 (2016) 2464-2470.

D. Basudhar, K. M. Miranda, D. A. Wink, L. A. Ridnour, Advances in Breast Cancer Therapy Using Nitric Oxide and Nitroxyl Donor Agents, in: 2016: pp. 377-403.

C. X. Qin, J. Anthonisz, C. H. Leo, N. Kahlberg, A. Velagic, M. Li, E. Jap, O. L. Woodman, L. J. Parry, J. D. Horowitz, B. K. Kemp-Harper, R. H. Ritchie, Nitric Oxide Resistance, Induced in the Myocardium by Diabetes, Is Circumvented by the Nitric Oxide Redox Sibling, Nitroxyl, Antioxid. Redox Signal. 32 (2020) 60-77.

F. L. M. Ricciardolo, P. J. Sterk, B. Gaston, G. Folkerts, Nitric Oxide in Health and Disease of the Respiratory System, Physiol. Rev. 84 (2004) 731-765.

V. L. Feigin, B. Norrving, M. G. George, J. L. Foltz, G. A. Roth, G. A. Mensah, Prevention of stroke: a strategic global imperative, Nat. Rev. Neurol. 12 (2016) 501-512.

A. G. Thrift, T. Thayabaranathan, G. Howard, V. J. Howard, P. M. Rothwell, V. L. Feigin, B. Norrving, G. A. Donnan, D. A. Cadilhac, Global stroke statistics, Int. J. Stroke. 12 (2017) 13-32.

J. Fukuto, P. Gulati, H. T. Nagasawa, Involvement of nitroxyl (HNO) in the cyanamide-induced vasorelaxation of rabbit aorta, Biochem. Pharmacol. 47 (1994) 922-924.

A. J. Väänänen, P. Salmenperä, M. Hukkanen, P. Rauhala, E. Kankuri, Cathepsin B is a differentiation-resistant target for nitroxyl (HNO) in THP-1 monocyte/macrophages, *Free Radic. Biol. Med.* 41 (2006) 120-131.

S. Adak, Q. Wang, D. J. Stuehr, Arginine conversion to nitroxide by tetrahydrobiopterin-free neuronal nitric-oxide synthase. Implications for mechanism., J. Biol. Chem. 275 (2000) 33554-61.

O. Sidorkina, M. G. Espey, K. M. Miranda, D. A. Wink, J. Laval, Inhibition of poly(ADP-RIBOSE) polymerase (PARP) by nitric oxide and reactive nitrogen oxide species, Free Radic. Biol. Med. 35 (2003) 1431-1438.

D. A. Wink, K. M. Miranda, T. Katori, D. Mancardi, D. D. Thomas, L. Ridnour, M. G. Espey, M. Feelisch, C. A. Colton, J. M. Fukuto, P. Pagliaro, D. A. Kass, N. Paolocci, Orthogonal properties of the redox siblings nitroxyl and nitric oxide in the cardiovascular system: a novel redox paradigm, Am. J. Physiol. Circ. Physiol. 285 (2003) H2264-H2276.

E. T. Chouchani, C. Methner, S. M. Nadtochiy, A. Logan, V. R. Pell, S. Ding, A. M. James, H. M. Cocheme, J. Reinhold, K. S. Lilley, L. Partridge, I. M. Feamley, A. J. Robinson, R. C. Hartley, R. A. J. Smith, T. Krieg, P. S. Brookes, M. P. Murphy, Cardioprotection by S-nitrosation of a cysteine switch on mitochondrial complex I., Nat. Med. 19 (2013) 753-759.

C. G. Tocchetti, B. A. Stanley, C. I. Murray, V. Sivakumaran, S. Donzelli, D. Mancardi, P. Pagliaro, W. D. Gao, J. van Eyk, D. A. Kass, D. A. Wink, N. Paolocci, Playing with Cardiac "Redox Switches": The "HNO Way" to Modulate Cardiac Function, Antioxid. Redox Signal. 14 (2011) 1687-1698.

J. C. Hartman, C. L. del Rio, J. E. Reardon, K. Zhang, H. N. Sabbah, Intravenous Infusion of the Novel HNO Donor BMS-986231 Is Associated With Beneficial Inotropic, Lusitropic, and Vasodilatory Properties in 2 Canine Models of Heart Failure, JACC Basic to Transl. Sci. 3 (2018) 625-638.

G. Keceli, A. Majumdar, C. N. Thorpe, S. Jun, C. G. Tocchetti, D. I. Lee, J. E. Mahaney, N. Paolocci, J. P. Toscano, Nitroxyl (HNO) targets phospholamban cysteines 41 and 46 to enhance cardiac function, J. Gen. Physiol. 151 (2019)

J. Parissis, V. Bistola, I. Ikonomidis, F. Triposkiadis, Nitroxyl donors for acute heart failure: promising newcomers, Eur. J. Heart Fail. 19 (2017) 1333-1334.

C. Tita, E. M. Gilbert, A. B. Van Bakel, J. Grzybowski, G. J. Haas, M. Jarrah, S. H. Dunlap, S. S. Gottlieb, M. Klapholz, P. C. Patel, R. Pfister, T. Seidler, K. B. Shah, T. Zieliński, R. P. Venuti, D. Cowart, S. Y. Foo, A. Vishnevsky, V. Mitrovic, A Phase 2a dose-escalation study of the safety, tolerability, pharmacokinetics and haemodynamic effects of BMS-986231 in hospitalized patients with heart failure with reduced ejection fraction, *Eur. J. Heart Fail.* 19 (2017) 1321-1332.

B. K. Kemp-Harper, J. D. Horowitz, R. H. Ritchie, Therapeutic Potential of Nitroxyl (HNO) Donors in the Management of Acute Decompensated Heart Failure, Drugs. 76 (2016) 1337-1348.

X. L. Ma, A. S. Weyrich, D. J. Lefer, A. M. Lefer, Diminished basal nitric oxide release after myocardial ischemia and reperfusion promotes neutrophil adherence to coronary endothelium., *Circ. Res.* 72 (1993) 403-412.

P. Pagliaro, D. Mancardi, R. Rastaldo, C. Penna, D. Gattullo, K. M. Miranda, M. Feelisch, D. A. Wink, D. A. Kass, N. Paolocci, Nitroxyl affords thiol-sensitive myocardial protective effects akin to early preconditioning, Free Radic. Biol. Med. 34 (2003) 33-43.

W. P. Arnold, C. K. Mittal, S. Katsuki, F. Murad, Nitric oxide activates guanylate cyclase and increases guanosine 3':5'-cyclic monophosphate levels in various tissue preparations, Proc. Natl. Acad. Sci. 74 (1977) 3203-3207.

D. Hirst, T. Robson, Nitrosative Stress as a Mediator of Apoptosis: Implications for Cancer Therapy, Curr. Pharm. Des. 16 (2010) 45-55.

K. Kashfi, Nitric oxide in cancer and beyond, Biochem. Pharmacol. 176 (2020) 114006.

A. J. Norris, M. R. Sartippour, M. Lu, T. Park, J. Y. Rao, M. I. Jackson, J. M. Fukuto, M. N. Brooks, Nitroxyl inhibits breast tumor growth and angiogenesis, Int. J. Cancer. 122 (2007) 1905-1910.

D. A. Stoyanovsky, N. F. Schor, K. D. Nylander, G. Salama, Effects of pH on the Cytotoxicity of Sodium Trioxodinitrate (Angeli's Salt), J. Med. Chem. 47 (2004) 210-217.

J. M. Fukuto, S. J. Carrington, HNO signaling mechanisms., Antioxid. Redox Signal. 14 (2011) 1649-1657.

E. G. DeMaster, B. Redfem, H. T. Nagasawa, Mechanisms of Inhibition of Aldehyde Dehydrogenase by Nitroxyl, the Active Metabolite of the Alcohol Deterrent Agent Cyanamide, *Biochem. Pharmacol.* 55 (1998) 2007-2015.

D. W. Shoeman, F. N. Shirota, E. G. DeMaster, H. T. Nagasawa, Reaction ofNitroxyl, an Aldehyde Dehydrogenase Inhibitor, with N-Acetyl-L-Cysteine, Alcohol. 20 (2000) 55-59.

P. Ramakrishnan Geethakumari, M. J. Schiewer, K. E. Knudsen, W. K. Kelly, PARP Inhibitors in Prostate Cancer, Curr. Treat. Options Oncol. 18 (2017) 37.

A. D. D'Andrea, Mechanisms of PARP inhibitor sensitivity and resistance, DNA Repair (Amst). 71 (2018) 172-176.

H.-J. Sun, S.-P. Xiong, Z.-Y. Wu, L. Cao, M.-Y. Zhu, P. K. Moore, J.-S. Bian, Induction of caveolin-3/eNOS complex by nitroxyl (HNO) ameliorates diabetic cardiomyopathy, Redox Biol. 32 (2020) 101493.

W.-W. Yew, D. P. Chan, A. Singhal, Y. Zhang, S.-S. Lee, Does oxidative stress contribute to adverse outcomes in HIV-associated TB?, J. Antimicrob. Chemother. 73 (2018) 1117-1120.

J. Galizia, M. A. Marti, Reactive nitrogen and oxygen species: Friend or foe in the tuberculosis fight, Tuberculosis. 113 (2018) 175-176.

M. Denis, Interferon-gamma-treated murine macrophages inhibit growth of tubercle bacilli via the generation of reactive nitrogen intermediates, Cell. Immunol. 132 (1991) 150-157.

H. Jamaati, E. Mortaz, Z. Pajouhi, G. Folkerts, M. Movassaghi, M. Moloudizargari, I. M. Adcock, J. Garssen, Nitric Oxide in the Pathogenesis and Treatment of Tuberculosis, Front. Microbiol. 8 (2017).

C. Porrini, N. Ramarao, S.-L. Tran, Dr. NO and Mr. Toxic—the versatile role of nitric oxide, Biol. Chem. 401 (2020) 547-572.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for generating nitroxyl (HNO) in the gas phase, the method comprising:

contacting a solid reducing agent with gaseous NO with heating to minimize dimerization of the HNO to $N_2O$ to form HNO in the gas phase.

2. The method of claim 1, wherein the solid reducing agent comprises an alcohol or a thiol or is a reducing inorganic solid.

3. The method of claim 2, wherein the solid reducing agent is selected from naringenin, $Ni^{+2}$-naringin, cysteine, and dithionite $(S_2O_4)^{2-}$.

4. The method of claim 2, wherein the contacting of the solid reducing agent and gaseous NO is done in the presence of one or more or $H_2O$, NaOH, $H_3PO_4$, and phosphate buffer.

5. The method of claim 1, further comprising monitoring the HNO in the gas phase directly or indirectly.

6. The method of claim 5, wherein the HNO in the gas phase is monitored directly by mass spectrometry or by an electrochemical HNO sensor.

7. The method of claim 5, wherein the HNO in the gas phase is monitored indirectly by monitoring nitrous oxide ($N_2O$) using infrared spectroscopy.

* * * * *